United States Patent [19]

Ackrell

[11] 4,000,288

[45] Dec. 28, 1976

[54] 6,11-DIHYDRODIBENZO-THIEPIN-11-ONES, COMPOSITIONS AND USES THEREOF

[75] Inventor: Jack Ackrell, Mexico City, Mexico

[73] Assignee: Syntex (U.S.A.) Inc., Palo Alto, Calif.

[22] Filed: Nov. 21, 1975

[21] Appl. No.: 634,085

Related U.S. Application Data

[63] Continuation-in-part of Ser. Nos. 550,316, Feb. 18, 1975, abandoned, and Ser. No. 591,725, June 30, 1975, abandoned, said Ser. No. 591,725, is a continuation-in-part of Ser. No. 550,316.

[52] U.S. Cl. .................... 424/267; 260/293.57; 260/327 B; 424/275
[51] Int. Cl.² ................................... C07D 337/12
[58] Field of Search ............ 260/327 B, 293.57; 424/275, 267

[56] References Cited

UNITED STATES PATENTS 3,946,036   3/1976   Gadient .................. 260/327 B

FOREIGN PATENTS OR APPLICATIONS 72-425   1/1972   Japan ..................... 260/327 B

OTHER PUBLICATIONS

Rajsner, et al., C.A. 79:78587x (1973).

*Primary Examiner*—Henry R. Jiles
*Assistant Examiner*—C. M. S. Jaisle
*Attorney, Agent, or Firm*—William B. Walker; Gerard A. Blaufarb

[57] ABSTRACT

This invention relates to novel 6,11-dihydrodibenzo-[b.e.]-thiepin-11-ones, methods of preparation, compositions and uses thereof.

26 Claims, No Drawings

6,11-DIHYDRODIBENZO-THIEPIN-11-ONES, COMPOSITIONS AND USES THEREOF

This application is a continuation-in-part of U.S. Pat. application Ser. No. 550,316, filed Feb. 18, 1975 and U.S. Application Ser. No. 591,725, filed June 30, 1975, both now abandoned said U.S. Application Ser. No. 591,725 also being a continuation-in-part of said U.S. Pat. Application Ser. No. 550,316.

DESCRIPTION OF THE INVENTION

This invention relates to novel 6,11-dihydrodibenzo [b.e.]-thiepin-11-ones selected from the group consisting of those having the formulas:

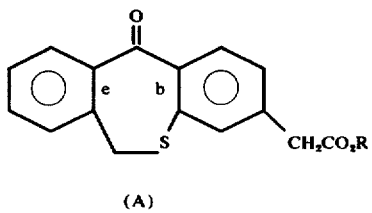

(A)

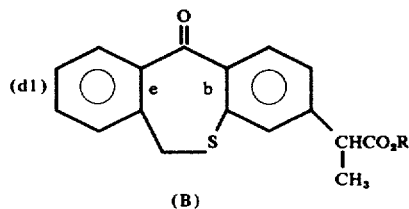

(B)

or the individual (d)-acid isomer or (1)-acid isomer of Formula (B), wherein R is hydrogen, and alkyl group containing from one to twelve carbon atoms, or a pharmaceutically acceptable salt thereof when R is hydrogen, or the said esters and pharmaceutically acceptable salts of the individual isomers of Formula B, and methods for the preparation thereof.

Also included in this invention are compositions and methods of use for the compounds of Formulas (A), (B), or the (d)-acid isomer of Formula (B), or the said esters and pharmaceutically acceptable salts of the (d)-acid isomer.

The term "alkyl" refers to and includes branched and straight chain hydrocarbons containing from one to twelve carbon atoms. Typical alkyl groups include methyl, ethyl, propyl, isopropyl, butyl, tertiary butyl, isoamyl, neopentyl, isopentyl, hexyl, octyl, nonyl, isodecyl, 6-methyldecyl, dodecyl, and the like.

The term "pharmaceutically acceptable salts" refers to salts prepared from pharmaceutically acceptable non-toxic bases including inorganic bases and organic bases. Salts derived from inorganic bases include sodium, potassium, lithium, ammonia, calcium, magnesium, ferrous, zinc, copper, maganous, aluminum, ferric, manganic salts and the like. Particularly preferred are the ammonia, potassium, sodium, calcium and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, tromethamine, lysine, arginine, histidine, caffeine, procaine, hydrabramine, choline, belaine, ethylenediamine, glucosamine, methylglucamine, theobromine, purines, piperazine, piperidine, N-ethylpiperidine, polyamine resins and the like. Particularly preferred organic non-toxic bases are isopropylamine, diethylamine, ethanolamine, piperidine, tromethamine, choline and caffeine.

The novel compounds of Formula (B), and Formulas (10), (11), (12) and (14) depicted below exist as pairs of optical isomers (or enantiomorphs), i.e., a (dl) mixture. However, each optical isomer as well as the (dl) mixtures thereof are included within the present invention.

When the novel compounds of this invention are to be used to elicite a physiological response (e.g., anti-inflammatory, analgesic and anti-pyretic activity), i.e., they are to be used as medicinals, a preferred sub-grouping is that of the compounds of Formulas (A) and (B), and the (d)-acid isomer of Formula (B) and the esters and pharmaceutically acceptable salts thereof.

A still further sub-grouping, for compounds to be used as medicinals are the compounds of Formula (B) and the (d)-acid isomer of Formula (B) and the esters and pharmaceutically acceptable salts thereof, and this sub-grouping may be divided into two further sub-groupings made up of (a) the compounds of Formula (B), i.e., the (dl)-compounds and (b) the (d)-acid isomer of Formula (B) and the esters and pharmaceutically acceptable salts thereof. The (1)-acid isomer of Formula (B) and the esters and pharmaceutically acceptable salts thereof are useful as intermediates for the preparation of the (dl)-acid of Formula (B), as described more fully below.

Japanese Patent Publication No. 425/72, published January 7, 1972, broadly discloses compounds of the formula:

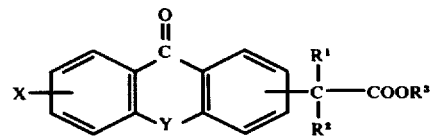

[wherein $R_1$, $R_2$ and $R_3$ are each a hydrogen atom or a lower alkyl group (e.g. methyl, ethyl, propyl and isopropyl); X is a hydrogen atom, a halogen atom (Cl, Br, I and F) or a lower alkyl group; and Y is an oxygen atom, -$CH_2S$ -, or

(wherein $R_4$ is a hydrogen atom or a lower alkyl group)] or the salt thereof; and specifically names in Example 3 thereof 11-oxo-6,11-dihydro-dibenzo [b.e.] thiepin-2-yl-acetic acid.

German OLS 24 42 060, laid open May 7, 1975, broadly discloses oxepin compounds of the formula:

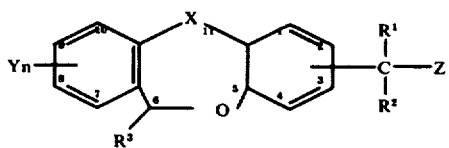

wherein X is C=O, CHCl, CHBr, $CH_2$, or $CHOR^4$; Y is alkyl of from 1 to 4 carbon atoms, alkoxy of from 1 to 4 carbon atoms, halogen or trifluoromethyl; n is an integer 0, 1, 2 or 3; Z is $COOR^5$, $CH_2OR^5$, $CONR_2^5$ or $CONHOR^5$; and $R^1$ to $R^5$ are hydrogen, or alkyl of from 1 to 4 carbon atoms.

Certain oxepin compounds are also disclosed in Belgian Patent No. 818,055, laid open November 18, 1974.

The novel compounds of my invention, namely, the compounds of Formulas (A) and (B), and the d-acid isomer of Formula (B) and the esters and pharmaceutically acceptable salts thereof, have markedly superior anti-inflammatory activity when compared with the closest prior art compounds of the Japanese patent (namely, 11-oxo-6,11-dihydrodibenzo[b.e.]thiepin-2-yl-acetic acid and 11-oxo-6,11-dihydrodibenzo[b.e.]thiepin-2-yl-propionic acid), using the carragenin rat paw assay (the assay referred to in the Japanese patent), as shown below.

The novel compounds of this invention are prepared according to the reaction scheme outlined in the flow sheets which follow:

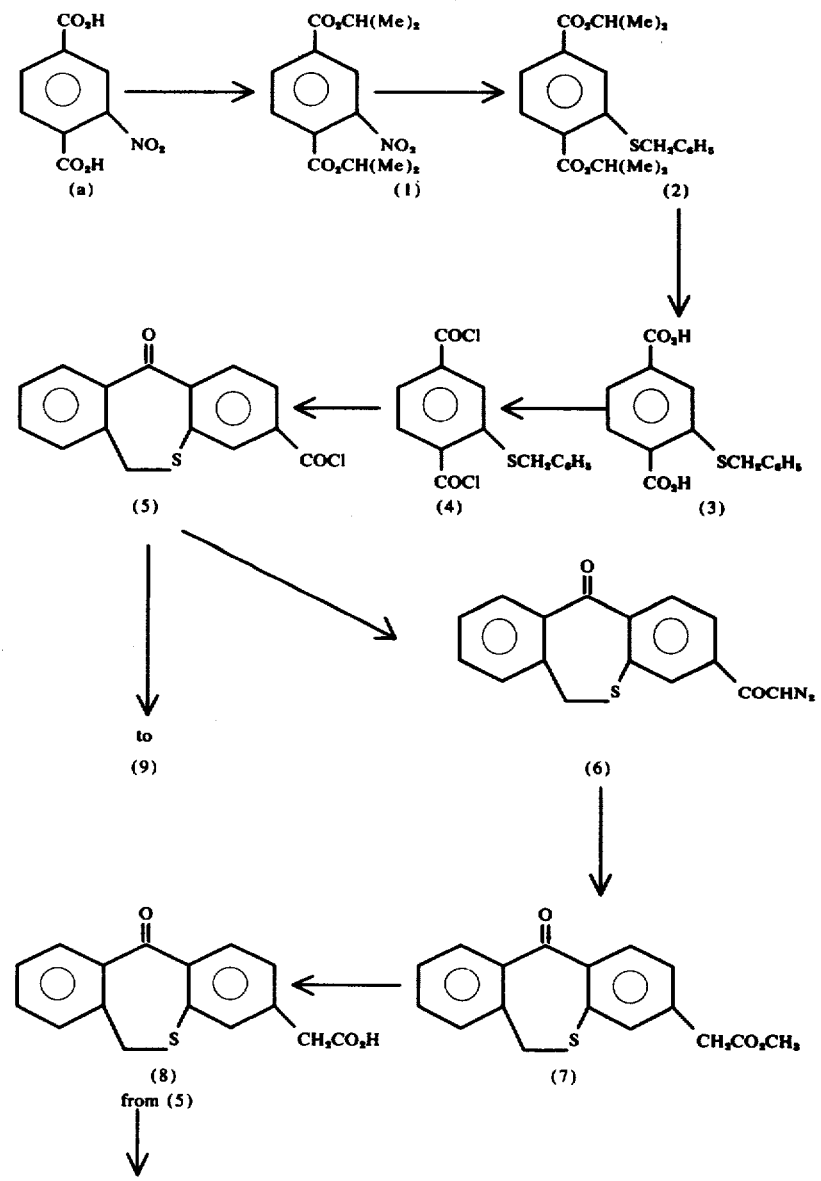

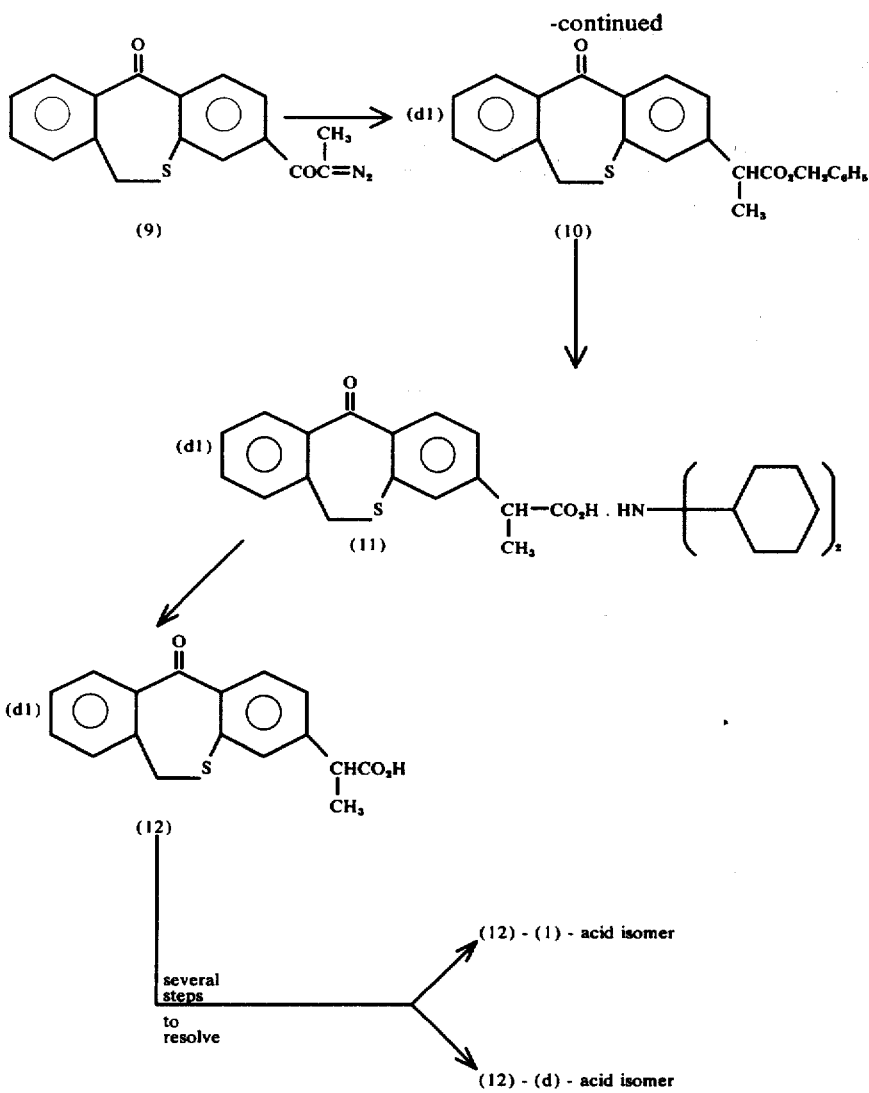

Diisopropyl nitroterephthalate (1) is prepared by esterifying nitroterephthalic acid (a) with isopropanol, the isopropanol serving both as reactant and solvent, in the presence of hydrogen chloride at a temperature of from about 25° C. to the reflux temperature of the reaction mixture for from about 48 to about 200 hours. Ordinarily, it is preferred to carry out the reaction at reflux for from about 48 to about 96 hours.

Diisopropyl nitroterepthalate (1) is then treated with benzyl mercaptan and sodium hydride in the presence of a suitable organic solvent, e.g., dimethylformamide, dimethylsulfoxide, and the like, at temperature of from about −40° C. to about 50° C., preferably, from about −35° C. to about 20° C., for from about 1 hour to about 10 hours preferably from about 2 hours to about 3 hours, to obtain diisopropyl (benzylthio)-terephthalate (2).

Base hydrolysis of (2) yields (benzylthio)-terephthalic acid (3). This reaction is carried out by treating (2) with a base, e.g., potassium hydroxide, sodium hydroxide, and the like, in the presence of water, and an organic solvent, e.g., methanol, ethanol, propanol, and the like, at a temperature of from about 40° C. to the reflux temperature of the reaction mixture, for from about 1 to about 12 hours. Preferably the hydrolysis reaction is carried out using aqueous methanolic potassium hydroxide at reflux temperature.

(Benzylthio)-terephthalyl chloride (4) is obtained by treating (3) with thionyl chloride at a temperature of from about 25° C. to the reflux temperature of the reaction mixture for about 1 to about 6 hours. It is preferred to carry out this reaction at reflux temperature.

The cyclization reaction by which (4) is converted to 6,11-dihydrodibenzo-[b.e.]-thiepin-11-one-3-carbonyl chloride (5) is carried out by treating (4) with nitromethane and aluminum chloride in the presence of a suitable organic solvent, e.g., methylene chloride, carbon disulfide, o-dichlorobenzene, and the like, at a temperature of from about 15° C. to about 35° C. for from about one-half to about 24 hours, preferably at from about 20° C. to about 25° C., for from about 4 to about 12 hours. The preferred solvent is methylene chloride.

The conversion of (5) to 3-diazoacetyl-6,11-dihydrodibenzo-[b.e.]-thiepin-11-one (6) carried out by treating (5) with diazomethane, in an organic solvent, e.g., methylene chloride, ether, carbon tetrachloride, and the like, or mixtures thereof, at a temperature of from about −20° C. to about 10° C., for from about 15 minutes to about 12 hours. Preferably this reaction is carried out at a temperature of from about −5° C. to about 5° C. for from about 15 to about 60 minutes.

The rearrangement of (6) to methyl 6,11-dihydrodibenzo-[b.e.]-thiepin-11-one-3-acetate (7) is carried out by intimately mixing (6) with methanol at a temperature of from about 50° C. to the reflux temperature of the mixture, followed by the addition, in portions, of a silver salt, e.g., silver benzoate, dissolved or suspended in a solvent, e.g., methanol or triethylamine. Likewise, other 3-esters, otherwise corresponding to (7) are obtained by substituting the appropriate alkyl alcohol, containing 2 to 12 carbon atoms, for methanol.

The hydrolysis of (7) to 6,11-dihydrodibenzo-[b.e.]-thiepin-11-one-3-acetic acid (8) is carried out by treating (7) with a base, e.g., potassium hydroxide, sodium hydroxide, sodium carbonate, and the like, in the presence of water and an organic solvent, e.g., methanol, ethanol, propanol, and the like, at a temperature of from about 0° C. to about 70° C. for from about 1 to about 24 hours. This hydrolysis reaction is preferably carried out using aqueous methanolic potassium hydroxide at a temperature of from about 20° C. to about 30° C. Likewise the other 3-esters, obtained as described above, are hydrolyzed to the 3-acetic acid (8). The temperature for the hydrolysis will depend on the particular ester to be hydrolyzed and thus can range from about 0° C. to reflux.

Treatment of 6,11-dihydrodibenzo-[b.e.]-thiepin-11-one-3-carbonyl chloride (5) with diazoethane in an organic solvent, e.g., ether, methylene chloride, carbon tetrachloride, and the like, at a temperature of from about −30° C. to about −10° C. is productive of 3-(α-diazopropionyl)-6,11-dihydrodibenzo-[b.e.]-thiepin-11-one (9). It is preferred to carry out this reaction using ethereal diazoethane at a temperature of from about −25° C. to about −20° C.

The rearrangement of (9) to benzyl (dl)-2-(6,11-dihydrodibenzo-[b.e.]-thiepin-11-one-3-yl) propionate (10) is carried out by treating (9) with a high boiling alcohol, e.g., benzyl alcohol, in the presence of an organic amine, e.g., collidine, quinoline, diethylaniline, and the like, at a temperature of from about 160° to about 190° C., for about one minute to about 1 hour, preferably from about 170° C. to about 175° C. for from about 2 to about 30 minutes.

To aid in the obtention of the free acid, (dl)-2-(6,11-dihydrodibenzo-[b.e.]-thiepin-11-one-3-yl) propionic acid (12), in purer form, (10) is first subjected to base hydrolysis as previously described above for the conversion of (7) to (8) [or (2) to (3)], followed by treatment with dicyclohexylamine to obtain dicyclohexylammonium (dl)-2-(6,11-dihydrodibenzo-[b.e.]-thiepin-11-one-3-yl) propionate (11).

The conversion of (11) to (dl)-2-(6,11-dihydrodibenzo-[b.e.]-thiepin-11-one-3-yl) propionic acid (12) is carried out by treating (11) in an organic solvent, e.g., methylene chloride, ether, benzene, and the like, with an acid salt or strong acid, e.g., sodium acid sulfate, hydrochloric acid, sulfuric acid, and the like, at a temperature of from about 0° C. to about 50° C., for from about 1 minute to about 1 hour, preferably from about 20° C. to about 25° C., for from about one to about five minutes.

Alternatively the compounds of Formula (12) are prepared as outlined in the following reaction scheme:

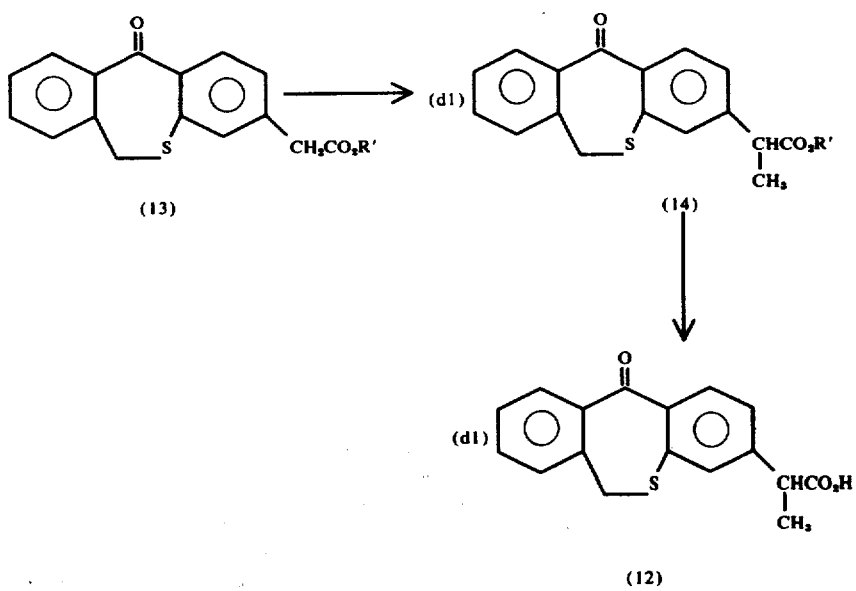

wherein R' is an alkyl group containing from 1 to 12 carbon atoms.

The α-methylation of the compounds of Formula (13), the esters of 6,11-dihydrodibenzo-[b.e.]-thiepin-11-one-3-acetic acid (R'=alkyl of $C_1$–$C_{12}$, preferably R'=methyl), to obtain the compounds of Formula (14), the esters of (dl)-2-(6,11-dihydrodibenzo-[b.e.]-thiepin-11-one-3-yl) propionic acid (R'=alkyl $C_1$–$C_{12}$, preferably R'=methyl), is carried out by treating the compounds of Formula (13) with an alkali metal hydrie, hydride, metal amide, alkali metal dialkylamide, and the like, such as sodium hydride, lithium diisopropylamide or sodium dimethylamide, in the presence of a polar non-protic solvent, e.g., N,N-dimethylacetamide, dimethylformamide, hexamethylphophoric triamide (HMPA), dimethylsulfoxide, sulfolane, and the like, at a temperature of from about 10° C. to about 60° C., followed by treatment with a methyl halide, e.g., methyl iodide, or a dialkyl sulfate, e.g., dimethyl sulfate, at a temperature of from about −15° to about 60° C., for from about 5 minutes to about 1 hour.

The compounds of Formula (14) are then hydrolyzed to the free acids of Formula (12), according to the method described above for the hydrolysis of the compound of Formula (7) to Formula (8).

Methods for the preparation of the compounds of Formula (13), wherein R' is $C_2$–$C_{12}$ alkyl are described fully below.

The (dl) mixture of (12) is separated into its respective d-isomer, (12)-(d)-acid isomer, and l-isomer, (12)-(l)-acid isomer, according to techniques known in the art, e.g., the resolution techniques set forth in Example 12B below.

Upon their preparation, the free acids of Formulas (8), (12), (12)-(d)-acid isomer and (12)-(l)-acid isomer, can be converted to their corresponding esters and acid addition salts.

The salt derivatives of the compounds of Formulas (8), (12), (12)-(d)-acid isomer, and (12)-(l)-acid isomer, are prepared by treating these free acids with an appropriate amount of a pharmaceutically acceptable base. Representative pharmaceutically acceptable bases are sodium hydroxide, potassium hydroxide, lithium hydroxide, ammonium hydroxide, calcium hydroxide, magnesium hydroxide, ferrous hydroxide, zinc hydroxide, copper hydroxide, manganous hydroxide, aluminum hydroxide, ferric hydroxide, manganic hydroxide, isopropylamine, trimethylamine, diethylamine, triethylamine, tripropylamine, ethanolamine, 2-dimethylaminoethanol, 2-diethylaminoethanol, tromethamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. The reaction is conducted in water, alone or in combination with an inert, water-miscible organic solvent, at a temperature of from about 0° C. to about 100° C., preferably at room temperature. Typical inert, water-miscible organic solvents include methanol, ethanol, isopropanol, butanol, acetone, dioxane or tetrahydrofuran. The molar ratio of compounds of Formulas (8), (12), (12)-(d)-acid isomer and (12)-(l)-acid-isomer, to base used are chosen to provide the ratio desired for any particular salt. For preparing, for example, the calcium salts or magnesium salts of the compounds of Formulas (A) and (B), and the individual (d)- and (l)-acid isomers of the latter, the free acid starting material of Formulas (8) (12), (12)-(d)-acid isomer and (12)-(l)-acid isomer, respectively, can be treated with at least one-half molar equivalent of pharmaceutically acceptable base to yield a neutral salt. When the aluminum salts of the compounds of Formulas (A) and (B), and the individual (d)- and (l)-acid isomers of the latter, are prepared, at least one-third molar equivalent of the pharmaceutically acceptable base are employed if a neutral salt product is desired.

In the preferred procedure, the calcium salts and magnesium salts of the compounds of Formulas (A) and (B), and the calcium and magnesium salts of the (d)- and (l)-acid isomers of Formula (B) can be prepared by treating the corresponding sodium or potassium salts of the compound of Formulas (A) and (B), and the sodium or potassium salts of the (d)- and (l)- acid isomers of Formula (B), with at least one-half molar equivalent of calcium chloride or magnesium chloride, respectively, in an aqueous solution, alone or in combination with an inert water-miscible organic solvent, at a temperature of from about 20° C. to about 100° C. Preferably, the aluminum salt of the compounds of Formulas (A) and (B), and the aluminum salt of the (d)- and (l)-acid isomers of Formula (B), can be prepared by treating the corresponding free acids of the compounds of Formulas (8), (12), (12)-(d)-isomer and (12)-(l)-isomer with at least one-third molar equivalent of an aluminum alkoxide, such as aluminum triethoxide, aluminum tripropoxide and the like, in a hydrocarbon solvent, such as benzene, xylene, cyclohexane, and the like at a temperature of from 20° C. to about115° C. Similar procedures can be used to prepare salts of inorganic bases which are not sufficiently soluble for easy reaction.

The salt products are isolated by conventional means. For example, the reaction mixtures are evaporated to dryness, and the salts can be further purified by conventional methods.

The salt derivatives of the compounds of Formulas (8), (12) and the salt derivatives of 12-(d)-acid isomer and 12-(l)-acid isomer, can be reconverted to their respective free acids by acidifying said salts with an acid, preferably an inorganic acid, e.g., hydrochloric acid, sulfuric acid, and the like, at temperature of from about 0° C. to about 30° C., preferably at room temperature.

The esters of Formulas (A) and (B), and the esters of the (d)-acid isomer and (l)-acid isomer of Formula (B), are prepared by esterifying the corresponding free acids of Formulas (8), (12), (12)-acid isomer and (12)-(l)-acid isomer, with an alcohol reagent corresponding to the desired ester, e.g., an alkanol having up to 12 carbon atoms. This reaction is conducted in the presence of a strong acid, such as boron trifluoride, hydrogen chloride, sulfuric acid, p-toluenesulfonic acid, and the like. If the alcohol reagent used in the esterification is a liquid at the reaction temperature, the alcohol reagent can be the reaction solvent. Optionally, the reaction can be carried out in an inert organic solvent in which the free acids of Formulas (8), (12), (12)-(d)-acid isomer and (12)-(l)-acid isomer, and the alcohol reagent are soluble, such as a hydrocarbon solvent, e.g., hexane, iso-octane, decane, cyclohexane, benzene, toluene, xylene; a halogenated hydrocarbon solvent, e.g., methylene chloride, chloroform, dichloroethane; or an ether solvent, e.g., diethyl ether, dibutyl ether, dioxane, tetrahydrofuran; and the like. In the case where the alcohol reagent is a solid, the reaction preferably is conducted in a non-aqueous liquid inert organic solvent. The reaction is conducted at from about 0° C. to the reflux temperature of the reaction mixture, preferably using hydrogen chloride at a temperature of from 15° C. to about 35° C.

The product is isolated by conventional means such as diluting the reaction mixture with water, extracting the resulting aqueous mixture with a water-immiscible inert organic solvent, such as diethyl ether, benzene, methylene chloride, and the like, combining the extracts, washing the extracts with water to neutrality and then evaporating under reduced pressure.

The preferred acid esters of Formulas (A) and (B), and the esters of the (d)-acid isomer and (l)-acid isomer of Formula (B), are those ester derivatives prepared from methyl alcohol, ethyl alcohol, propyl alcohol, isopropyl alcohol, butyl alcohol, 2-butyl alcohol, isoamyl alcohol, pentyl alcohol, 2-pentyl alcohol, isopentyl alcohol, hexyl alcohol, 2-hexyl alcohol, isohexyl alcohol, heptyl alcohol, 2-heptyl alcohol, isoheptyl alcohol, octyl alcohol, 2-octyl alcohol, isooctyl alcohol, nonyl alcohol, 2-nonyl alcohol, isononyl alcohol, decyl alcohol, 2-decyl alcohol, isodecyl alcohol, undecyl alcohol, dodecyl alcohol, and the like.

Alternatively, the esters of Formulas (A) and (B), and the esters of the (d)-acid isomer and (l)-acid isomer of Formula (B), can be prepared by transesterification, according to methods known in the art. It is preferred in preparing the esters via transesterification to go from a lower ester to a higher ester, e.g., from the methyl ester, for example, to the isoamyl ester, for example. However, by using a substantial excess of a lower alcohol, a higher ester can be transesterified to a lower ester; thus, for example, by using a substantial excess of ethanol, the hexyl ester is converted by the transesterification to the ethyl ester.

The (12)-(l)-acid isomer, (l)-2-(6,11-dihydrodibenzo-[b.e.]-thiepin-11-one-3-yl) propionic acid, and the corresponding esters and salts thereof, are converted to (dl)-2-(6,11-dihydrodibenzo-[b.e.]-thiepin-11-one-3-yl) propionic acid (12) by treatment with an excess of a strong base, e.g., sodium hydroxide, potassium hydroxide, tetramethylammonium hydroxide, and the like, at a temperature of from about 60° C. to the reflux temperature of the reaction mixture for from about 4 to about 10 hours, under an inert atmosphere, e.g., nitrogen, followed by acidification with a mineral acid, e.g., hydrochloric acid, sulfuric acid, and the like. When the above reaction is carried out on the (12)-(l)-acid isomer or salts thereof, water is the preferred solvent. When the reaction is carried out on the esters of the (12)-(l)-acid isomer the preferred solvent is an aqueous alkanol, e.g., aqueous methanol.

The compounds of Formulas (A) and (B), and the (d)-acid isomer of Formula (B) and the esters and pharmaceutically acceptable salts thereof, are useful as anti-inflammatory agents, platelet aggregation inhibitors, fibrinolytic agents, and as smooth muscle relaxants. The compounds of Formulas (A) and (B), and the (d)-acid isomer of Formula (B) and the esters and pharmaceutically acceptable salts thereof, can be used both prophylactically and therapeutically.

The compounds of Formulas (A) and (B), and the (d)-acid isomer of Formula (B) and the esters and pharmaceutically acceptable salts thereof, exhibit anti-inflammatory, analgesic and anti-pyretic activities. Accordingly, the compositions containing these compounds are useful in the treatment and elimination of inflammation such as inflammatory conditions of the muscular skeletal system, skeletal joints and other tissues, for example, in the treatment of inflammatory conditions such as rheumatism, concussion, laceration, arthritis, bone fractures, post-traumatic conditions, and gout. In those cases in which the above conditions include pain and pyrexia coupled with inflammation, the instant compounds are useful for the relief of these conditions as well as the inflammation.

Administration of the active compound of Formula (A) and (B), and the (d)-acid isomer of Formula (B) and the esters and pharmaceutically acceptable salts thereof, in an appropriate pharmaceutical composition can be via any of the accepted modes of administration of agents for the treatment of inflammation, pain, or pyrexia, or the propylaxis thereof. Thus, administration can be for example, orally, parenterally, or topically, in the form of solid, semi-solid or liquid dosage forms, such as, for example, tablets, suppositories, pills, capsules, powders, liquids, suspensions, creams, lotions, ointments, or the like, preferably in unit dosage forms suitable for simple administration of precise dosages. The compositions will include a conventional pharmaceutical carrier or excipient and an active compound of Formulas (A) or (B), or the (d)-acid isomer of Formula (B) and the esters and pharmaceutically acceptable salts thereof, and, in addition, may include other medicinal agents, pharmaceutical agents, carriers, adjuvants, etc.

The preferred manner of administration, for the conditions detailed above, is oral using a convenient daily dosage regimen which can be adjusted according to the degree of affliction. Generally, a daily dose of from 0.05 mg. to ten mg. of the active compound of Formulas (A) and (B), and the (d)-acid isomer of Formula (B) and the esters and pharmaceutically acceptable salts thereof, per kilogram of body weight is used. Most conditions respond to treatment comprising a dosage level of the order of 0.25 mg. to three mg. per kilogram of body weight per day. For such oral administration, a pharmaceutically acceptable non-toxic composition is formed by the incorporation of any of the normally employed excipients, such as, for example, pharmaceutical grades of mannitol, lactose, starch, magnesium stearate, sodium saccharin, talcum, cellulose, glucose, sucrose, magnesium carbonate, and the like. Such compositions take the form of solutions, suspensions, tablets, pills, capsules, powders, sustained release formulations and the like.

The active compound of Formulas (A) and (B), and the (d)-acid isomer of Formula (B) and the esters and pharmaceutically acceptable salts thereof, may be formulated into a suppository using, for example, polyalkylene glycols, for example, polypropylene glycol, as the carrier. Liquid pharmaceutically administerable compositions can, for example, be prepared by dissolving, dispersing, etc. an active compound, as described above, and optional pharmaceutical adjuvants in a carrier, such as, for example, water, saline, aqueous dextrose, glycerol, ethanol, and the like, to thereby form a solution or suspension. If desired, the pharmaceutical composition to be administered may also contain minor amount of non-toxic auxiliary substances such as wetting or emulsifying agents, pH buffering agents and the like, such as for example, sodium acetate, sorbitan monolaurate, triethanolamine oleate, etc.

Actual methods of preparing such dosage forms are known, or will be apparent, to those skilled in this art; for example, see Remington's Pharmaceutical Sciences, Mack Publishing Company, Easton, Pennsylvania, 14th. Edition, 1970. The composition to be administered will, in any event, contain a quantity of the active compound(s) in a pharmaceutically effective amount for relief of the particular condition being treated in accordance with the teachings of this invention.

The compounds of Formulas (A) and (B), and the (d)-acid isomer of Formula (B) and the esters and pharmaceutically acceptable salts thereof, described above, are also uterine smooth muscle relaxants and thus are useful as agents for maintaining the pregnancy of pregnant mammals, for the benefit of the mother and/or the fetus, until termination of the pregnancy is considered, from a medical point of view, to be favorable, or more favorable, for the mother and/or the fetus. It should be understood, however, that in certain instances, for example where parturition has already begun (i.e., the mother is experiencing uterine contractions, especially near full term), that administration of the compounds herein described may not maintain the pregnant state for an indefinite period of time. Rather, in such instances, the pregnancy will, most probably, be slightly "prolonged", a factor which may be advantageous to either the mother and/or the fetus.

In particular, the compounds of Formulas (A) and (B), and the (d)-acid isomer of Formula (B) and the esters and pharmaceutically acceptable salts thereof, are used as agents for delaying the onset of, or for postponing, parturition. As used in this application, the phrase "to delay the onset of parturition" is intended to cover that delay in parturition caused by the administration of the compounds of Formulas (A) and (B), and the (d)-acid isomer of Formula (B) and the esters and pharmaceutically acceptable salts thereof, at any time before uterine muscle contractions have begun. Thus, it is intended that the aforementioned phrase cover abortion prevention early in pregnancy (i.e., before the fetus is "viable") as well as delaying premature parturition, a term which sometimes is used with reference to that premature labor experienced later in the pregnancy when the fetus is considered to be viable. In either case, the agents are administered as prophylactic agents in that such administration tends to prevent the onset of parturition. This administration is particularly useful in the treatment of women having a history of spontaneous abortion, miscarriage or premature delivery (i.e., delivery prior to full term). Such administration is also useful where there are clinical indications that the pregnancy might be terminated prior to that time and is considered favorable to the mother and/or fetus.

With respect to animals, this treatment can also be utilized to synchronize the deliveries from a group of pregnant animals to happen at or about the same time, or to happen at or about a desired time and/or place, when the births can be handled with greater facility.

As used in this application, the phrase "postponing parturition" is intended to cover that delay in parturition caused by the administration of the compounds of Formulas (A) and (B), and the (d)-acid isomer of Formula (B) and the esters and pharmaceutically acceptable salts thereof after uterine muscle contractions have begun. The condition of the patient, including the time within the gestation period when the contractions have begun, the severity of the contractions and how long the contractions have taken place will affect the results achieved with the administration of the compounds of Formulas (A) and (B), and the (d)-acid isomer of Formula (B) and the esters and pharmaceutically acceptable salts thereof. For example, the effect can be to reduce the intensity and/or the duration of the contractions (the actual act of parturition being "prolonged"), or to stop the contractions altogether. In either case, the effect will be to prolong the gestation period although, depending upon the condition of the patient as described above, the effect may either be slight or, under appropriate circumstances, somewhat greater. Such administration may be to prevent spontaneous abortion, to cause the delivery to be more easily accomplished and/or less painful to the mother, or to occur at a more appropriate time and/or place.

In all cases, administration of the compounds of Formulas (A) and (B), and the (d)-acid isomer of Formula (B) and the esters and pharmaceutically acceptable salts thereof, for the purposes set forth herein, should be consistent with best and/or accepted medical (or veterinary) practices so as to maximize the benefits to the mother and the fetus. For example, administration should not be continued so long past full term that the fetus dies in utero.

In the practice of the methods of the present invention, a therapeutically effective amount of a compound of Formulas (A) and (B), and the (d)-acid isomer of Formula (B) and the esters and pharmaceutically acceptable salts thereof, or a pharmaceutical composition containing a compound of Formulas (A) and (B), and the (d)-acid isomer of Formula (B) and the esters and pharmaceutically acceptable salts thereof, is administered to the pregnant mammal via any of the usual and acceptable methods known in the art. The compound can be administered either singly or in combination with another compound or compounds, as defined above, or other pharmaceutical agents, carriers, adjuvants, etc. Such compound(s) or compositions can be administered orally, parenterally, either in the form of solid, semi-solid, or liquid dosage forms. Typically, administration is by a pharmaceutical composition containing the pharmaceutically active compound and one or more pharmaceutical carriers or adjuvants.

The administerable pharmaceutical composition may take the form of oral tablets, vaginal or urterine tablets or suppositories, pills, capsules, liquid solutions, suspensions, or the like, preferably in unit dosage forms suitable for simple administration of precise dosages. Conventional non-toxic solid carriers include, for example, pharmaceutical grades of mannitol, lactose, starch, magnesium stearate, sodium saccharin, talcum, cellulose, glucose, sucrose, magnesium carbonate, and the like. The active compound as defined above may be formulated as suppositories using, for example, polyalkylene glycols, for example polypropylene glycol, as the carrier. Liquid pharmaceutically administerable compositions can, for example, be prepared by dissolving, dispersing, etc. an active compound as defined above and optional pharmaceutical adjuvants in a carrier, such as, for example, water, saline, aqueous dextrose, glycerol, ethanol, and the like, to thereby form a solution or suspension. If desired, the pharmaceutical composition to be administered may also contain minor amounts of non-toxic auxiliary substances such as wetting or emulsifying agents, pH buffering agents and the like, for example, sodium acetate, sorbitan monolaurate, triethanolamine oleate, etc. Actual methods of preparing such dosage forms are known, or will be apparent, to those skilled in this art; for example, see Remington's Pharmaceutical Sciences, Mack Publishing company, Easton, Pa., 14th. Edition, 1970. The composition or formulation to be administered will, in any event, contain a quantity of the active compound(s) in an amount effective to delay the onset of parturition or to postpone parturition if uterine contractions have already begun. Generally a daily dose of from five mg. to about 250 mg. of the active compound per kilogram of body weight will be administered, with administration being a single daily dose or up to three or four smaller doses regularly given throughout the day. The amount of active compound administered will, of course, depend on its relative activity.

DESCRIPTION OF SPECIFIC EMBODIMENTS

The following specific description, recited in the examples below, is given to enable those skilled in this art to more clearly understand and practice the present invention. It should not be considered as a limitation upon the scope of the invention but merely as being illustrative and representative thereof.

Where necessary, examples are repeated to prepare additional material for later examples; and unless otherwise specified, the reactions are carried out at room temperature (20° to 30° C.).

EXAMPLE 1

200 G. of nitroterephthalic acid (a) was dissolved in 1 liter of isopropanol and the thus-obtained solution was saturated with hydrogen chloride and refluxed for 3 days. (During this period, hydrogen chloride was passed into the solution occasionally in order to maintain the concentration thereof.) The reaction solution was then cooled and the isopropanol was removed by evaporation under reduced pressure to give a residue which was dissolved in 500 ml. of methylene chloride. The resultant solution was washed with 10% aqueous sodium carbonate, and the organic layer obtained was dried over magnesium sulfate, followed by removal of the solvent in vacuo to give 245 g. (yield 87.5%)of diisopropyl nitroterephthalate (1), an oil; IR: $\nu_{max.}^{CHCl_3}$ 1724, 1542, 1350 cm.$^{-1}$; NMR: $\delta_{TMS}^{CDCl_3}$ 1.35 (6H, d), 1.40 (6H, d), 5.24 (1H, 7 lines), 5.27 (1H, 7 lines), 7.71 (1H, d), 8.24 (1H, dd), 8.43 ppm (1H, d).

EXAMPLE 2

5.1 G. of sodium hydride was slowly added to a cooled (−20° C.) solution of 23.5 ml. of benzyl mercaptan in 100 ml. of dimethylformamide. The resultant solution was cooled to −30° C. and there was added thereto 53 g. of diisopropyl nitroterephthalate (1) in 100 ml. of dimethylformamide. After 1 hour at −30° C. and 2 hours at 0° C., the reaction mixture was poured into water, the precipitate was filtered off, washed with water and dried to yield 77–92% of crude diisopropyl-(benzylthio)-terephthalate (2), a sample of which, following recrystallization from pentane, melted at 70°–71° C.

EXAMPLE 3

The crude diisopropyl-(benzylthio)-terephthalate (2) obtained in Example 2 was refluxed with 500 ml. methanol, 25 g. of potassium hydroxide and 50 ml. of water for 2 hours. The reaction mixture was then concentrated to a small volume, cooled, diluted with water and filtered through diatomaceous earth (Celite). The thus-obtained filtrate was acidifiled with 4N hydrochloric acid and the precipitate which formed was collected by filtration and dried in an oven at 90°–100° C. to yield 45 g. (87%) of (benzylthio)-terephthalic acid (3) having a melting point of 299°–300° C.

EXAMPLE 4

10 G. of (benzylthio)-terephthalic acid (3) was treated with 10 ml. of thionyl chloride and the reaction mixture was refluxed for 4 hours. After removal of the excess thionyl chloride in vacuo, the residue obtained was slurried with hexane and the solid product was filtered off to yield 10.2 g. (92%) of (benzylthio)-terephthalyl chloride (4) having a melting point of 158° C.

EXAMPLE 5

10.2 G. of (benzylthio)-terephthalyl chloride (4) in 100 ml. of methylene chloride was added to a solution of 14.75 g. of aluminium chloride in 100 ml. of methylene chloride containing 10.51 ml. of nitromethane. After 5 hours at 25° C., 16.5 ml. of saturated aqueous sodium chloride was added with vigorous stirring. The inorganic salts which precipitated were filtered off and the filtrate was evaporated to dryness to give a solid residue which was slurried with ether. The ether slurry was filtered to yield 7.0 g. (70.7%) of 6,11-dihydrodibenzo-[b.e.]-thiepin-11-one-3-carbonyl chloride (5) having a melting point of 119°–120° C.

EXAMPLE 6

A solution of 11 g. of 6,11-dihydrodibenzo-[b.e.]-thiepin-11-one-3-carbonyl chloride (5) in 100 ml. of methylene chloride was slowly added to excess diazomethane (prepared) from 20 g. N-nitroso N-methylurea) in 200 ml. of ether solution. After 2 hours the reaction mixture was concentrated to about 50 ml. by boiling off the solvent, followed by cooling. The cooled reaction mixture was filtered to yield a residue of 9.5 g. (85%) of 3-diazoacetyl-6,11-dihydrodibenzo-[b.e.]-thiepin-11-one (6) having a melting point of 153° C., with decomposition.

EXAMPLE 7

9.5 G. of 3-diazoacetyl-6,11-dihydrodibenzo-[b.e.]-thiepin-11-one (6) was suspended in 500 ml. of methanol and the suspension was stirred vigorously and refluxed. 2 G. of silver benzoate suspended in 20 ml. of methanol was added in 2 ml. portions over 50 minutes. The reaction mixture was refluxed for 15 hours, cooled and the solvent removed at the pump and following chromatography of the residue on 400 g. of silica gel there was obtained 7 g. of methyl 6,11-dihydrodibenzo-[b.e.]-thiepin-11-one-3-acetate (7) having a melting point (ether) of 100°–101° C.

Similarly, by substituting other alkyl alcohols, containing 2 to 12 carbon atoms, for methanol, in the procedure of this Example there are obtained, for example, ethyl 6,11-dihydrodibenzo-[b.e.]-thiepin-11-one-3-acetate,
propyl 6,11-dihydrodibenzo-[b.e.]-thiepin-11-one-3-acetate,
isopropyl 6,11-dihydrodibenzo-[b.e.]-thiepin-11-one-3-acetate,
hexyl 6,11-dihydrodibenzo-[b.e.]-thiepin-11-one-3-acetate,
nonyl 6,11-dihydrodibenzo-[b.e.]thiepin-11-one-3-acetate,
dodecyl 6,11-dihydrodibenzo-[b.e.]-thiepin-11-one-3-acetate, and the like.

EXAMPLE 8

7.0 G. of methyl 6,11-dihydrodibenzo-[b.e.]-thiepin-11-one-3-acetate (7) was stirred with 200 ml. of methanol and a solution of 2.0 g. of potassium hydroxide in 5 ml. of water was added. After one hour, the solution was clarified by filtration and the filtrate was acidified with 3N aqueous hydrochloric acid and diluted with 400 ml. of water. The precipitated solid was filtered off, dried in an oven at about 80° C. and recrystallized from benzene:hexane to yield 5.6 g. of 6,11-dihydrodibenzo-[b.e.]-thiepin-11-one-3-acetic acid (8) having a melting point of 154°–155° C.

Similarly, 6,11-dihydrodibenzo-[b.e.]-thiepin-11-one-3-acetic acid is obtained by substituting, in place of methyl 6,11-dihydrodibenzo-[b.e.]-thiepin- 11-one-3-acetate, the other 3-esters obtained in Example 7, for example ethyl 6,11-dihydrodibenzo-[b.e.]-thiepin-11-one-3-acetate, propyl 6,11-dihydrodibenzo-[b.e.]-thiepin-11-one-3-acetate, isopropyl 6,11-dihydrodibenzo-[b.e.]-thiepin-11-one-3-acetate, hexyl 6,11-dihydrodibenzo-[b.e.]-thiepin-11-one-3-acetate, nonyl 6,11-dihydrodibenzo-[b.e.]-thiepin-11-one-3-acetate, dodecyl 6,11-dihydrodibenzo-[b.e.]-thiepin-11-one-3-acetate, and the like.

EXAMPLE 9

A solution of 2.5 g. of 6,11-dihydrodibenzo-[b.e.]-thiepin-11-one-3-carbonyl chloride (5) in 30 ml. of methylene chloride was added to a solution of diazoethane (prepared from 20 g. N-ethyl N-nitrosourea) in 150 ml. of ether at −20° C. The reaction mixture was allowed to warm to room temperature and most of the solvent was blown off in a stream of nitrogen, followed by filtration to yield 1.5 g. of 3-(α-diazopropionyl)6,11-dihydrodibenzo-[b.e.]-thiepin-11-one (9) having a melting point of 127° C., with decomposition.

EXAMPLE 10

1.1 G. of 3-(α-diazopropionyl)-6,11-dihydrodibenzo-[b.e.]-thiepin-11-one (9) suspended in 3 ml. of collidine was added to a mixture of 5 ml. of benzyl alcohol and 5 ml. of collidine maintained at 170°-175° C. After five minutes, the reaction mixture was cooled and the solvents were distilled off in vacuo, followed by chromatography of the residue on silica gel to yield 1.0 of g. of benzyl (dl)-2-(6,11-dihydrodibenzo-[b.e.]-thiepin-11-one-3-yl) propionate (10), a colorless oil; IR: $\nu_{max.}^{CHCl_3}$ 1735, 1640, 1600 cm.$^{-1}$; NMR: $\delta_{TMS}^{CDCl_3}$ 1.50 (3H, d), 3.66 (1H, q), 4.0 (2H, s), 5.07 (2H, s), 7.0–7.6 (6H, m), 8.10 ppm (1H, dd); MS: 388 (M$^+$).

EXAMPLE 11

1.0 G. of benzyl (dl)-2-(6,11-dihydrodibenzo-[b.e.]-thiepin-11-one-3-yl) propionate (10) in 25 ml. of methanol was treated with 0.3 g. of potassium hydroxide in two ml. of water. After 1 hour, the reaction mixture was poured into 25 ml. of 3N hydrochloric acid and 100 ml. of water. The resultant mixture was extracted with ethyl acetate and the organic layer was then extracted with 10% aqueous sodium carbonate solution. The basic aqueous layer was acidified with 3N hydrochloric acid and the precipitated acid, (dl)-2-(6,11-dihydrodibenzo-[b.e.]-thiepin-11-one-3-yl) propionic acid, was extracted with ether. The ether layer was evaporated after drying over magnesium sulfate to yield an oil which was taken up in five ml. of benzene. The benzene solution was treated with 0.5 g. of dicyclohexylamine and the solution was allowed to crystallize overnight, followed by drying to yield 640 mg. of dicyclohexylammonium (dl)-2-(6,11-dihydrodibenzo-[b.e.]-thiepin-11-one-3-yl) propionate (11) having a melting point of 163°-165° C.

EXAMPLE 12

640 Mg. of dicyclohexylammonium (dl)-2-(6,11-dihydrodibenzo-[b.e.]-thiepin-11-one-3-yl) propionate (11) was dissolved in 10 ml. of methylene chloride and the solution was stirred for 15 minutes with an excess of sodium acid sulfate monohydrate (1.0 g.). The reaction mixture was filtered and the solvent was removed in vacuo. The residue was extracted with ether. Evaporation of the ether extracted yielded an oil which on drying under high vacuum (0.1 mm) gave 300 mg. of (dl)-2-(6,11-dihydrodibenzo-[b.e.]-thiepin-11-one-3-yl) propionic acid (12), as a foam, having an IR: $\nu_{max.}^{KBr}$ 3,700–2,500, 1710, 1640 cm.$^{-1}$; NMR: $\delta_{TMS}^{CDCl_3}$ 1.47 (3H, d), 3.68 (1H, q), 4.00 (2H, s), 7.0–8.0 (6H, m), 8.10 ppm (1H, d); MS: 298 M$^+$).

Dicyclohexylammonium (dl)-2-(6,11-dihydrodibenzo-[b.e.]-thiepin-11-one-3-yl) propionate (11) was obtained in several runs according to the procedure described in Example 11. The products obtained from these runs were combined and treated according to the procedure of Example 12 to yield a foam which was crystallized from diethyl ether:hexane (2:1) to yield (dl)-2-(6,11-dihydrodibenzo-[b.e.]-thiepin-11-one-3-yl) propionic acid (12), having a melting point of 113°-115° C., and the same IR, NMR and MS as set forth above in this Example 12.

EXAMPLE 12A

To 4.0 g. of sodium hydride (100%) in 600 ml. of N,N-dimethylacetamide, under a nitrogen atmosphere, there was added 41 g. of methyl 6,11-dihydrodibenzo-[b.e.]-thiepin-11-one-3-acetate (13, R' = methyl), a deep red color developing. The mixture was stirred at room temperature overnight, followed by the rapid addition of 20.0 g. of methyl iodide. The thus-obtained reaction mixture, which had turned from red to greenblue, was stirred at room temperature for 15–20 minutes, poured into, and shaken with, a mixture of 6 l. of saturated sodium chloride solution, 600 ml. water and 2 l. of ethyl acetate. The layers were allowed to separate and the organic layer was successively washed with 3 300 ml. portions of saturated sodium chloride solution. The saturated sodium chloride solution washes were successively extracted with 3 300 ml. portions of ethyl acetate. The ethyl acetate extracts were combined, dried over sodium sulfate and evaporated to dryness under vacuum to yield 46.0 g. of a dark yellow residue comprising methyl (dl)-2-(6,11-dihydrodibenzo-[b.e.]-thienpin-11-one-3-yl) propionate (14; R' = methyl), which was combined with 25.0 g of similar material previously obtained, using the same alkylation procedure. The combined residues (71.0 g.) were percolated over 1 kg. of silical gel, followed by elution with methylene chloride and finally with ethyl acetate:-methylene chloride (2:98). The eluted fractions which, by thin layer chromatography, predominantly showed the presence of the α-methylated product, were combined, and evaporated to dryness to yield 62.0 g. of a more pure pale yellow powder comprising methyl (dl)-2-(6,11-dihydrodibenzo-[b.e.]-thiepin-11-one-3-yl) propionate (14, R' = methyl), [a sample of methyl (dl)-2-(6,11-dihydrodibenzo-[b.e.]-thiepin-11-one-3-yl) propionate (14, R' = methyl), obtained by the same procedure, after crystallization from diethyl ether had the following physical constants: melting point 62.0°-62.5° C.; IR: $\nu_{max.}^{KBr}$ 3,700–2,500, 1,740, 1,640 cm.$^{-1}$; NMR: $\delta_{TMS}^{CDCl_3}$ 1.47 (3H, d), 3.65 (3H, s), 3.68 (1H, q), 4.02 (2H, s) 7.0–8.0 (6H, m), 8.21 ppm (1H, d); MS: 312 (M$^+$), which was dissolved in a mixture of 1600 ml. of tetrahydrofuran and 800 ml. of water. To the thus-obtained solution there was added 180 ml. of 1N sodium hydroxide and the reaction mixture was stirred for 3 hours, followed by removal of tetrahydrofuran under vacuum, and dilution with 3 of water. The dilute basic solution was extracted with two 600 ml. portions of ethyl acetate, followed by acidification of the aqueous layer with 2N hydrochloric acid. The acidified aqueous solution was extracted several times with methylene chloride. The methylene chloride extracts were combined, dried over sodium sulfate and evaporated to dryness to give a residue which was taken up in 250 ml. of diethyl ether and allowed to crystallize. The fine white crystals which formed were filtered, washed with ice-cold diethyl ether, and sucked dry to yield 40.0 g. of (dl)-2-(6,11-dihydrodibenzo-[b.e.]-thiepin-11-one-3-yl) propionic acid (12), having a melting point of 114.5°–115.5° C. (uncorrected), IR: $\nu_{max}^{KBr}$ 3,700–2,500, 1,710, 1,655 cm.$^{-1}$; NMR:$\delta_{TMS}^{CDCl_3}$ 1.47 (3H, d), 3.68 (1H, q), 4.00 (2H, s), 7.0–8.0 (6H, m), 8.12 ppm (1H, d); MS: 298 (M$^+$).

Similarly substituting other 3-esters of 6,11-dihydrodibenzo-[b.e.]-thiepin-11-one-3-acetic acid, e.g.

ethyl 6,11-dihydrodibenzo-[b.e.]-thiepin-11-one-3-acetate, propyl 6,11-dihydrodibenzo-[b.e.]-thiepin-11-one-3-acetate, isoamyl 6,11-dihydrodibenzo-[b.e.]-thiepin-11-one-3-acetate, hexyl 6,11-dihydrodibenzo-[b.e.]-thiepin-11-one-3-acetate, nonyl 6,11-dihydrodibenzo-[b.e.]-thiepin-11-one-3-acetate, dodecyl 6,11-dihydrodibenzo-[b.e.]-thiepin-11-one-3-acetate, and the like, for methyl 6,11-dihydrodibenzo-[b.e.]-thiepin-11-one-3-acetate, is productive of (dl)-2-6,11-dihydrodibenzo-[b.e.]-thiepin-11-one-3-yl) propionic acid.

EXAMPLE 12B a. 5.0 G. of (dl)-2-(6,11-dihydrodibenzo-[b.e.]-thiepin-11-one-3-yl) propionic acid (12) was dissolved in 50 ml. of benzene containing 5 ml. of thionyl chloride and 3 drops of dimethylformamide and stirred for 1½ hours. The reaction mixture was evaporated to an oily residue which was dissolved in 50 ml. of dry benzene and re-evaporated to give an oily residue comprising (dl)-2-(6,11-dihydrodibenzo-[b.e.]-thiepin-11-one-3-yl) propionyl chloride. This oily residue was dissolved in 250 ml. of acetonitrile and 10 ml. of (1)-1-phenylethylamine and 6.5 ml. of triethylamine were added thereto. After stirring for 2 hours the reaction mixture was added to 750 ml. of water and extracted with 400 ml. of ethyl acetate. The thus-obtained organic extract was washed with 400 ml. of 2N hydrochloric acid, dried and evaporated, to yield a residue which was chromatographed on 400 g. of silica gel, eluting with benzene:ethyl acetate (10:1) to obtain firstly 3.3 g. of the less polar (1)-2-(6,11-dihydrodibenzo-[b.e.]-thiepin-11-one-3-yl) propionyl (1)-1-phenylethylamide, which after recrystallization from ethyl acetate:hexane (1:2) had a melting point of 162°–163° C. and an [α]$_D$ +16.4° (10 mg./ml., chloroform); and secondly 2.8 g. of the more polar (d)-2-(6,11-dihydrodibenzo-[b.e.]-thiepin-11-one-3-yl) propionyl (1)-1-phenylethylamide, which after recrystallization from ethyl acetate:hexane (1:2), had a melting point of 170°–171°C. and an [α]$_D$ −1.4° (10 mg./ml. chloroform.).

b. 3.0 G. of (d)-2-(6,11-dihydrodibenzo-[b.e.]-thiepin-11-one-3yl) propionyl (1)-1-phenylethylamide in 93 ml. of concentrated hydrochloric acid and 62 ml. of acetic acid was heated for 8 hours at 87° C. The mixture was cooled, poured into water and extracted with 250 ml. of ethyl acetate. The ethyl acetate extract was washed with water and extracted with 250 ml. of 0.5 molar aqueous sodium carbonate. The ethyl acetate solution remaining following the aqueous sodium carbonate extraction was dried and evaporated to give 1.06 g. of unchanged phenylethylamide starting material. The aqueous sodium carbonate extract was acidified with 500 ml. of 2N hydrochloric acid and extracted with 350 ml. of ethyl acetate. The ethyl acetate extract was dried and evaporated to give 1.34 g. of a residue comprising 2-(6,11-dihydrodibenzo-[b.e.]-thiepin-11-one-3-yl) propionic acid. The 1.06 g. of recovered phenylethylamide starting material was dissolved in 45 ml. of concentrated hydrochloric acid and 30 ml. of acetic acid, and heated for 14 hours at 85° C., followed by working up as described above to afford 0.86 g. of a residue comprising 2-(6,11-dihydrodibenzo-[b.e.]-thiepin-11-one-3-yl) propionic acid which was combined with the 1.34 g. obtained above. The combined acid residues (2.2 gm.) were dissolved in 10 ml. of isopropanol and 0.95 gm. of 1-amphetamine was added. The solution was cooled to −10° C. and left for 4 hours and filtered to yield 2.69 g. of a residue which was shaken with 100 ml. of 2N hydrochloric acid and 100 ml. of ethyl acetate. The separated organic layer was dried over magnesium sulfate and evaporated to yield 1.90 g. of a residue which was dissolved in 9 ml. of isopropanol, followed by the addition of 0.86 g. of 1-amphetamine. The solution was cooled to −10° C. and left for 2 hours, followed by filtration to yield 2.53 g. of a residue which was shaken with 100 ml. of 2N hydrochloric acid and 100 ml. of ethyl acetate. The organic layer was separated, dried over magnesium sulfate, and evaporated to give 1.80 g. of a residue which was dissolved in 8 ml. of isopropanol followed by the addition of 0.86 g. of 1-amphetamine. The solution was cooled to −10° C. and left for 2 hours, followed by filtration to yield 2.46 g. of a residue which was shaken with 100 ml. of 2N hydrochloric acid and 100 ml. of ethyl acetate. The organic layer was separated, dried over magnesium sulfate, and evaporated to give 1.75 g. of a residue which was dissolved in 7 ml. of isopropanol, followed by the addition of 0.83 g. of 1-amphetamine. The solution was cooled to −10° and left for 16 hours followed by filtration, to yield 2.40 g. of a residue which was shaken with 100 ml. of hydrochloric acid and 100 ml. of ethyl acetate. The separated organic layer was washed, dried over magnesium sulfate, and evaporated to give 1.647 g. of (d)-2-(6,11-dihydrodibenzo-[b.e.]-thiepin-11-one-3-yl) propionic acid [(12)-(d)-acid isomer], as a gum, having an [α]$_D$ + 37.2° (5 mg./ml., chloroform); NMR: $\delta_{TMS}^{CDCl_3}$ 1.48 (3H, d), 3.68 (1H, q), 4.01 (2H, s), 7.0–7.6 (6H, m) 8.15 ppm (1H, d), MS: 298 (M$^+$) 265, 253.

c. 2.64 G. of (1)-2-(6,11-dihydrodibenzo-[b.e.]-thiepin-11-one-3-yl) propionyl (1)-1-phenylethylamide was dissolved in 21 ml. of acetic acid and 111 ml. of acetic anhydride and the solution cooled to 0° C. 9.25 G. of sodium nitrite was added in 4 portions over 1 hour. The mixture was stirred at 0° C. for 5 hours and then at room temperature for 17 hours. 250 Ml. of water and 100 ml. of ethyl acetate were added and the mixture stirred vigorously for 1½ hours, followed by dilution with 500 ml. of water and extracted with 400 ml. of ethyl acetate. The organic extract was washed, dried over magnesium sulfate, evaporated and the residue obtained refluxed for 1 hour in 50 ml. of benzene. The benzene solution was cooled, washed with 100 ml. of 0.5 molar aqueous potassium carbonate, dried over magnesium sulfate, and evaporated. The residue thus-obtained was chromatographed on 100 g. of silica gel, eluting with benzene, to yield 0.75 g. of (1)-2-(6,11-dihydrodibenzo-[b.e.]-thiepin-11-one-3-yl) propionic acid 1-phenylethanol ester, as an oil; NMR: $\delta_{TMS}^{CDCl_3}$ 1.29–1.52 (6H, m), 3.68 (1H, q), 4.02 (2H, s), 7.0–7.6 (11H, m), 8.16 ppm (1H, m). 0.74 G. of the 1-phenylethanol ester was then stirred in 10 ml. of benzene and 10 ml. of trifluoroacetic acid for 2 hours, followed by the addition of 200 ml. of water and extracted with 200 ml. of ethyl acetate. The organic extract was washed, dried over magnesium sulfate, and evaporated to give 0.51 g. of (1)-2-(6,11-dihydrodibenzo-[b.e.]-thiepin-11-one-3-yl) propionic acid [(12)-(1)-acid isomer] as a gum, having an $[\alpha]_D$ −37.8° (5 mg./ml., chloroform) and the same NMR and MS set forth for the corresponding (d)-compound [(12)-(d)-acid isomer] in part (b) of this example.

EXAMPLE 13

250 Mg. of 6,11-dihydrodibenzo-[b.e.]-thiepin-11-one-3-acetic acid (8) was dissolved in 30 ml. of isoamyl alcohol and the solution was saturated with hydrogen chloride. After 90 minutes, the excess alcohol was distilled off in vacuo and the residue was purified by preparative thin layer chromatography [silica gel; ethyl acetate:hexane (1:9)] to yield 171 mg. of isoamyl 6,11-dihydrodibenzo-[b.e.]-thiepin-11-one-3-acetate, which after crystallization from methylene chloride/hexane had a melting point of 91°–92° C.

Likewise other esters, e.g., methyl, ethyl, propyl, isopropyl, hexyl, nonyl, dodecyl, and the like, of 6,11-dihydrodibenzo-[b.e.]-thiepin-11-one-3-acetic acid (8) are obtained by substituting other alcohols, e.g., methyl, ethyl, propyl, isopropyl, hexyl, nonyl, dodecyl alcohol and the like, for isoamyl alcohol.

EXAMPLE 14

150 Mg. of (dl)-2-(6,11-dihydrodibenzo-[b.e.]-thiepin-11-one-3-yl) propionic acid (12) was dissolved in five ml. of methanol and the solution was saturated with hydrogen chloride. After 24 hours, the excess alcohol was distilled off in vacuo and the residue was purified by chromatography on silica gel [eluant:ethyl acetate:hexane (1:8)] to yield 120 mg. of methyl (dl)-2-(6,11-dihydrodibenzo-[b.e.]-thiepin-11-one-3-yl) propionate, an oil, having a UV: $\lambda_{max}^{dioxane}$ 250, 350nm ($\epsilon$ 21,200, 2950); IR: $\nu_{max}^{CHCl_3}$ 1,740, 1,645, 1,600 cm.$^{-1}$; NMR: $\delta_{TMS}^{CDCl_3}$ 1.48 (3H, d), 3.60 (3H, s), 4.0 (2H, s), 7.0–7.6 (6H, m), 8.10 ppm (1H, dd).

Similarly, substituting the (12)-(d)-acid isomer, (d)-2-(6,11-dihydrodibenzo-[b.e.]-thiepin-11-one-3-yl) propionic acid, or the corresponding (12)-(1)-acid isomer, for the (dl)-mixture, is productive of the methyl ester of (d)-2-(6,11-dihydrodibenzo-[b.e.]-thiepin-11-one-3-yl) propionic acid, or the corresponding methyl ester of the (12)-(1)-acid isomer, respectively.

EXAMPLE 15

300 Mg. of (dl)-2-(6,11-dihydrodibenzo-[b.e.]-thiepin-11-one-3-yl) propionic acid (12) was dissolved in 5 ml. of isoamyl alcohol and the solution was saturated with hydrogen chloride. After 24 hours, the excess alcohol was distilled off in vacuo and the residue was purified by chromatography on alumina to yield 350 mg. of isoamyl (dl)-2-(6,11-dihydrodibenzo-[b.e.]-thiepin-11-one-3-yl) propionate, an oil, having a UV: $\lambda_{max}^{CH_3OH}$ 245, 350nm ($\epsilon$ 19,700, 2240); IR: $\nu_{max}^{CHCl_3}$ 1,730, 1,650, 1,600 cm.$^{-1}$; NMR: $\delta_{TMS}^{CDCl_3}$ 0.80 (6H, d), 1.45 (6H, d+m), 3.70 (2H, m), 4.0 (2H, s), 7.0–7.6 (6H, m), 8.1 ppm (1H, dd).

Likewise other esters, e.g., ethyl, propyl, isopropyl, hexyl, nonyl, dodecyl, and the like, of (dl)-2-(6,11-dihydrodibenzo-[b.e.]-thiepin-11-one-3-yl) propionic acid (12) are obtained by substituting other alcohols, e.g., ethyl, propyl, isopropyl, hexyl, nonyl, dodecyl alcohol, and the like, for isoamyl alcohol.

Similarly, by substituting the (12)-(d)-acid isomer, (d)-2-(6,11-dihydrodibenzo-[b.e.]-thiepin-11-one-3-yl) propionic acid, or the corresponding (12)-(1)-acid isomer, for the (dl)-mixture, with the appropriate alcohol there is obtained the isoamyl, ethyl, propyl, isopropyl, hexyl, nonyl, dodecyl, and the like, esters of (d)-2-(6,11-dihydrodibenzo-[b.e.]thiepin-11-one-3-yl) propionic acid, or the corresponding esters of the (12-(1)-acid isomer, respectively.

EXAMPLE 16

300 Mg. of 6,11-dihydrodibenzo-[b.e.]-thiepin-11-one-3-acetic acid (8) in five ml. of methanol was titrated with 1N methanolic potassium hydroxide to a faint orange color. The color was discharged by the addition of 3 mg. of solid 6,11-dihydrodibenzo-[b.e.]-thiepin-11-one-3-acetic acid. The solvent was evaporated in vacuo and the residue taken up in 2 ml. of methanol, followed by precipitation with ether to yield 335 mg. of crude potassium 6,11-dihydrodibenzo-[b.e.]-thiepin-11-one-3-acetate which, after recrystallization from isopropanol, had a melting point of 206°–208° C. (dec.).

Likewise other salts, e.g., ammonium and sodium, of 6,11-dihydrodibenzo-[b.e.]-thiepin-11-one-3-acetic acid (8) are prepared by substituting ammonium hydroxide and sodium hydroxide for potassium hydroxide.

EXAMPLE 17

150 Mg. of (dl)-2-(6,11-dihydrodibenzo-[b.e.]-thiepin-11-one-3-yl) propionic acid (12) in one ml. of methanol was titrated with 1N methanolic potassium hydroxide to a faint orange color. A small amount of solid (dl)-2-(6,11-dihydrodibenzo-[b.e.]-thiepin-11-one-3-yl) propionic acid was added to decolorize the solution. The solvent was stripped and 5 ml. of toluene was added. The thus obtained toluene solution was evaporated to dryness to give a solid, which was dried at 100° C. in vacuo to yield 158 mg. of potassium (dl)-2-(6,11-dihydrodibenzo-[b.e.]-thiepin-11-one-3-yl) propionate, softening at 120° C. and having a melting point of 145°–155° C. This solid on exposure to moist air melted and resolidified to yield 175 mg. of the dihydrate of potassium (dl)-2-(6,11-dihydrodibenzo-[b.e.]-thiepin-11-one-3-yl) propionate, having a melting point of 88°–90° C.

Likewise other salts, e.g., ammonium and sodium, of (dl)-2-(6,11-dihydrodibenzo-[b.e.]-thiepin-11-one-3-yl) propionic acid (12) are prepared by substituting, e.g., ammonium hydroxide and sodium hydroxide for potassium hydroxide.

Similarly, by substituting the (12)-(d)-acid isomer, (d)-2-(6,11-dihydrodibenzo-[b.e.]-thiepin-11-one-3-yl) propionic acid, or the corresponding (12)-(1)- acid isomer, for the (dl)-mixture, with the appropriate hydroxide, there is obtained the potassium, ammonium, and sodium salts of (d)-2-(6,11-dihydrodibenzo-[b.e.]-thiepin-11-one-3-yl) propionic acid, or the corresponding salts of the (12)-(1)-acid isomer, respectively.

EXAMPLE 18

300 Mg. of 6,11-dihydrodibenzo-[b.e.]-thiepin-11-one-3-acetic acid (8) was dissolved in an excess of 1N aqueous sodium hydroxide and the resultant solution was buffered with 0.3 g. of ammonium chloride. The buffered solution was added to a solution of 200 mg. calcium carbonate in 1N aqueous hydrochloric acid. The precipitate which formed was collected by filtration, washed consecutively with water, dimethoxyethane and ether, to yield 180 mg. of calcium 6,11-dihydrodibenzo-[b.e.]-thiepin-11-one-3-acetate having a melting point of 220–225° C. (dec.), softens >205° C.).

Likewise magnesium 6,11-dihydrodibenzo-[b.e.]-thiepin-11-one-3-acetate is prepared by substituting magnesium carbonate for calcium carbonate.

EXAMPLE 19

175 Mg. of (dl)-2-(6,11-dihydrodibenzo-[b.e.]-thiepin-11-one-3-yl) propionic acid (12) in 5 ml. of methanol was titrated with 1N methanolic potassium hydroxide to a faint orange color, followed by discharging the color by the addition of three mg. of solid (dl)-2-(6,11-dihydrodibenzo-[b.e.]-thiepin-11-one-3-yl) propionic acid, yielding a solution containing potassium (dl)-2-(6,11-dihydrodibenzo-[b.e.]-thiepin-11-one-3-yl) propionate. A solution of 40 mg. of calcium carbonate dissolved in the minimum amount of 1N hydrochloric acid necessary to effect solution of the calcium carbonate, was buffered with 100 mg. of solid ammonium chloride, followed by the further addition of five ml. of water. The thus obtained buffered calcium solution was then added to the solution of potassium (dl)-2-(6,11-dihydrodibenzo-[b.e.]-thiepin-11-one-3-yl) propionate to yield a precipitate. The precipitate was collected, washed with water and dried at room temperature to yield 160 mg. of calcium (dl)-2-(6,11-dihydrodibenzo-[b.e.]-thiepin-11one-3yl) propionate, softening at 150°C. and having a melting point of 160°165°C.

Likewise magnesium (dl)-2-(6,11-dihydrodibenzo-[b.e.]-thiepin-11-one-3-yl) propionate is prepared by substituting magnesium carbonate for calcium carbonate.

Similarly, by substituting the (12)-(d)-acid isomer, (d)-2-(6,11-dihydrodibenzo-[b.e.]-thiepin-11-one-3-yl) propionic acid, or the corresponding (12)-(1)-aicd isomer, for the (dl)-mixture with the appropriate carbonate, there are obtained the calcium and magnesium salts of (d)-2-(6,11-dihydrodibenzo-[b.e.]-thiepin-11-one-3-yl) propionic acid, or the corresponding salts of the (12)-(1)-acid isomer, respectively.

EXAMPLE 20

200 Mg. of 6,11-dihydrodibenzo-[b.e.]-thiepin-11one-3-acetic acid (8) in one ml. of methanol was titrated with 1N methanolic potassium hydroxide to a faint orange color. A small amount of solid 6,11-dihydrodibenzo-[b.e.]-thiepin-11-one-one-3-acetic acid was added to decolorize the solution. The solvent was stripped and the residue was dissolved in 5 ml. of water. The thus obtained aqueous solution of potassium 6,11-dihydrodibenzo-[b.e.]-thiepin-11-one-3-acetate was added to a solution of 150 mg. of cupric nitrate trihydrate in 5 ml. of water. The precipitate which formed was collected, washed with water and dried in air to yield 200 mg. of copper 6,11-dihydrodibenzo-[b.e.]-thiepin-11-one-3-acetate, sintering a 139–140°C. and having a melting point of 155–160°C.

EXAMPLE 21

200 Mg. of (dl)-2-(6,11-dihydrodibenzo-[b.e.]-thiepin-11-one-3yl) propionic acid (12) in one ml. of methanol was titrated with 1N methanolic potassium hydroxide to a faint orange color. A small amount of solid (dl)-2-(6,11-dihydrodibenzo-[b.e.]-thiepin-11one-3-yl) propionic acid was added to decolorize the solution. The solvent was stripped and the residue was dissolved in 5 ml. of water. The thus obtained aqueous solution of potassium (dl)-2-(6,11-dihydrodibenzo-[b.e.]-thiepin-11-one-3-yl) propionate was added to a solution of 150 mg. of cupric nitrate trihydrate in 5 ml. of water. The precipitate which formed was collected, washed with water and dried in air to yield 200 mg. of copper (dl)-2-(6,11-dihydrodibenzo-[b.e.]-thiepin-11one-3yl) propionate, sintering at 140° C. and having a melting point of 160–165° C.

Similarly, substituting the (12)-(d)-acid isomer, (d)-2-(6,11-dihydrodibenzo-[b.e.]-thiepin-11one-3-yl) propionic acid, or the corresponding (12)-(1)-acid isomer, for the (dl)-mixture, is productive of the copper salt of (d)-2-(6,11-dihydrodibenzo-[b.e.]-thiepin-11one-3-yl) propionic acid, or the corresponding copper salt of the (12) -(1)-acid isomer, respectively.

EXAMPLE 22

200 Mg. of 6,11-dihydrodibenzo-[b.e.]-thiepin-11-one-3-acetic acid (8) in 15 ml. of hot benzene was treated with 60 mg. of isopropylamine. The solution was allowed to cool to room temperature and the product was filtered off, washed with ether and dried to yield 217 mg. of isopropylammonium 6,11-dihydrodibenzo-[b.e.]-thiepin-11-one-3-acetate having a melting point of 147–148° C.

Likewise other salts, e.g., amine salts, such as, diethylamine, ethanolamine, piperidine, tromethamine, choline, and caffeine, of 6,11-dihydrodibenzo-[b.e.]-thiepin-11-one-3-acetic acid (8) are prepared by substituting each of the respective amines for isopropylamine.

EXAMPLE 23

193 Mg. of (dl)-2-(6,11-dihydrodibenzo-[b.e.]-thiepin-11-one-3-y1) propionic acid (12) in ten ml. of benzene was treated with 60 mg. of piperidine. The solution obtained was allowed to stand for 1 hour and the crystalline material which formed was filtered, washed with ether and air dried to yield 183 mg. of piperidinium (dl)-2-(6,11-dihydrodibenzo-[b.e.]-thiepin-11one-3-yl) propionate, a sample of which, following recrystallization from benzene had a melting point of 140–141° C.

Likewise other salts, e.g., amine salts, e.g., isopropylamine, diethylamine, ethanolamine, tromethamine, choline, and caffeine, of (dl)-2-(6,11-dihydrodibenzo-[b.e.]-thiepin-11-one-3-yl) propionate are prepared by substituting each of the respective amines for piperidine.

Similarly, substituting the (12)-(d)-acid isomer, (d)-2-(6,11-dihydrodibenzo-[b.e.]-thiepin-11-one-3-yl) propionic acid, or the corresponding (12)-(1)-acid isomer, for the (dl)-mixture, with the appropriate amine, is productive of the amine salts, e.g., piperidine, isopropylamine, diethylamine, ethanolamine, tromethamine, choline and caffeine, of (d)-2-(6,11-dihydrodibenzo-[b.e.]-thiepin-11-one-3-yl) propionic acid, or the corresponding (12)-(1)-acid isomer amine salts thereof, respectively.

EXAMPLE 24

One g. of potassium 6,11-dihydrodibenzo-[b.e.]-thiepin-11-one-3-acetate is dissolved in 50 ml. of water and the solution is acidified with 20 ml. of 3N aqueous hydrochloric acid. The reaction mixture is extracted twice with ethyl acetate (25 ml. portions) and the extracts are combined, washed with 50 ml. of water and dried over magnesium sulfate. The solvent is evaporated under reduced pressure and the residue is recrystallized from benzene to yield 6,11-dihydrodibenzo-[b.e.]-thiepin-11-one-3-acetic acid (8).

Similarly, other salts, e.g., sodium, ammonium, calcium, amine, and the like, of 6,11-dihydrodibenzo-[b.e.]-thiepin-11-one-3-acetic acid are converted to 6,11-dihydrodibenzo-[b.e.]-thiepin-11-one-3-acetic acid.

In like manner, substituting the salts, e.g., potassium, sodium, ammonium, calcium, amine, and the like, of (dl)-2-(6,11-dihydrodibenzo-[b.e.]-thiepin-11-one-3-yl) propionic acid, (d)-2-(6,11-dihydrodibenzo-[b.e.]-thiepin-11-one-3-yl) propionic acid, and the corresponding (1)-acid isomer salts thereof, respectively, is productive of (dl)-2-(6,11-dihydrodibenzo-[b.e.]-thiepin-11-one-3-yl) propionic acid, (d)-2-(6,11-dihydrodibenzo-[b.e.]-thiepin-11-one-3-yl) propionic acid, and the corresponding (1)-acid isomer thereof, respectively.

EXAMPLE 25

One g. of methyl 6,11-dihydrodibenzo-[b.e.]-thiepin-11-one-3-acetate (7) was dissolved in 500 ml. of toluene containing 5 g. of n-octanol and 0.5 g. of p-toluenesulfonic acid. The reaction mixture was heated in a nitrogen atmosphere and a total of 350 ml. of toluene was slowly distilled out over a period of 5 hours. The reaction mixture was cooled and concentrated to about 10 ml. by evaporation under reduced pressure. The residue was then chromatographed on 200 g. of silica gel eluting with hexane:ethyl acetate (1:8) to yield octyl 6,11-dihydrodibenzo-[b.e.]-thiepin-11-one-3-acetate.

Similarly, other lower esters (e.g., the propyl ester) of 6,11-dihydrodibenzo-[b.e.]-thiepin-11-one-3-acetic acid can be transesterified to a higher ester (e.g., the decyl ester) of 6,11-dihydrodibenzo-[b.e.]-thiepin-11-one-3-acetic acid.

In like manner lower esters (e.g., the methyl ester) of (dl)-2-(6,11-dihydrodibenzo-[b.e.]-thiepin-11-one-3-yl) propionic acid, (d)-2-(6,11-dihydrodibenzo-[b.e.]-thiepin-11-one-3-yl) propionic, or the corresponding (1)-acid isomer lower esters thereof, are converted to the higher esters (e.g., the octanyl ester) of (dl)-2-(6,11-dihydrodibenzo-[b.e.]-thiepin-11-one-3-yl) propionic acid, (d)-2-(6,11-dihydrodibenzo-[b.e.]-thiepin-11-one-3-yl) propionic, or the corresponding (1)-acid isomer higher ester thereof, respectively.

EXAMPLE 26

Five hundred mg. of dodecyl 6,11-dihydrodibenzo-[b.e.]-thiepin-11-one-3-acetate was refluxed with 250 ml. of absolute ethanol containing 10 mg. of sodium cyanide for 18 hours in a nitrogen atmosphere. The reaction mixture was cooled and evaporated under reduced pressure to yield a residue which was chromatographed on 100 g. of silica gel eluting with hexane: ethyl acetate (1:8) to yield ethyl 6,11-dihydrodibenzo-[b.e.]-thiepin-11-one-3-acetate.

Similarly, other higher esters (e.g., the nonyl ester) of 6,11-dihydrodibenzo-[b.e.]-thiepin-11-one-3-acetic acid can be transesterified to a lower ester (e.g., the hexyl ester) of 6,11-dihydrodibenzo-[b.e.]-thiepin-11one-3-acetic acid.

In like manner, higher esters (e.g., the dodecyl ester) of (dl)-2-(6,11-dihydrodibenzo-[b.e.]-thiepin-11-one-3-yl) propionic acid are converted to the lower esters (e.g., the ethyl ester) of (dl)-2-(6,11-dihydrodibenzo-[b.e.]-thiepin-11-one-3-yl) propionic acid.

EXAMPLE 27

0.05 G. of (1)-2-(6,11-dihydrodibenzo-[b.e.]-thiepin-11one-3-yl) propionic acid [(12)-(1)-acid isomer] was refluxed, under nitrogen, in 6 ml. of water containing 0.07 g. of sodium hydroxide for 7 hours. The reaction solution was cooled, acidified with 5 ml. of 2N hydrochloric acid and extracted with 15 ml. of ethyl acetate. The extract was washed with 15 ml. of water, dried with magnesium sulfate, and evaporated to yield 0.041 g. of (dl)-2-(6,11-dihydrodibenzo-[b.e.]-thiepin-11-one-3-yl) propionic acid (12), a gum, having an $[\alpha]_D -.80 \pm 1.0°$ (5 mg./ml. chloroform); NMR: $\delta_{TMS}^{CDCl_3}$ 1.47 (3H, d), 3.70 (1H, g), 7.0–7.6 (6H, m), 8.13 ppm (1H, d); MS 298 (M$^+$265, 253.

EXAMPLE 28

| Ingredients | Quantity per tablet, mgs. |
|---|---|
| 6,11-dihydrodibenzo-[b.e.]-thiepin-11-one-3-acetic acid | 150 |
| cornstarch | 40 |
| sucrose | 200 |

The above ingredients are thoroughly mixed and pressed into single scored tablets.

EXAMPLE 29

| Ingredients | Quantity per tablet, mgs. |
|---|---|
| (dl)-2-(6,11-dihydrodibenzo-[b.e.]-thiepin-11-one-3-yl) propionic acid | 25 |
| cornstarch | 100 |
| lactose | 393 |
| magnesium stearate | 2 |

The above ingredients are mixed intimately and pressed into single scored tablets.

12.5 Mg. of (d)-2-(6,11-dihydrodibenzo-[b.e.]-thiepin-11-one-3-yl) propionic acid is substituted for the 25 mg. of the (dl) compound of the above composition.

EXAMPLE 30

| Ingredients | Quantity per capsule, mgs. |
|---|---|
| potassium 6,11-dihydrodibenzo-[b.e.]-thiepin-11-one-3-acetate | 150 |
| lactose | 190 |

The above ingredients are mixed and introduced into a hard-shell gelatin capsule.

EXAMPLE 31

| Ingredients | Quantity per capsule, mgs. |
|---|---|
| calcium 6,11-dihydrodibenzo-[b.e.]-thiepin-11-one-3-acetate | 150 |
| lactose | 182 |
| magnesium stearate | 8 |

The above ingredients are mixed and introduced into a hard-shell gelatin capsule.

EXAMPLE 32

| Ingredients | Quantity per tablet, mgs. |
|---|---|
| isopropylammonium 6,11-dihydrodibenzo-[b.e.]-thiepin-11-one-3-acetate | 150 |
| cornstarch | 100 |
| lactose | 370 |
| magnesium stearate | 2 |

The above ingredients are mixed intimately and pressed into single scored tablets.

EXAMPLE 33

| Ingredients | Quantity per capsule, mgs. |
|---|---|
| methyl 6,11-dihydrodibenzo-[b.e.]-thiepin-11-one-3-acetate | 25 |
| lactose | 225 |

The above ingredients are mixed and introduced into a No. 1 hard-shell gelatin capsule.

EXAMPLE 34

| Ingredients | Quantity per tablet, mgs. |
|---|---|
| 6,11-dihydrodibenzo-[b.e.]-thiepin-11-one-3-acetic acid | 150 |
| sucrose | 245 |

The above ingredients are thoroughly mixed and processed into single scored tablets, one tablet being administered every 3 to 4 hours.

EXAMPLE 35

| Ingredients | Quantity per tablet, mgs. |
|---|---|
| isoamyl 6,11-dihydrodibenzo-[b.e.]-thiepin-11-one-3-acetate | 200 |
| cornstarch | 100 |
| lactose | 368 |

-continued

| Ingredients | Quantity per tablet, mgs. |
|---|---|
| magnesium stearate | 2 |

The above ingredients are mixed intimately and pressed into single scored tablets.

EXAMPLE 36

| Ingredients | Quantity per capsule, mgs. |
|---|---|
| (dl)-2-(6,11-dihydrodibenzo-[b.e.]-thiepin-11-one-3-yl) propionic acid | 25 |
| lactose | 225 |
| detrose | 10 |

The above ingredients are mixed and introduced into a hard-shell gelatin capsule.

12.5 Mg. of (d)-2-(6,11-dihydrodibenzo-[b.e.]-thiepin-11-one-3-yl) propionic acid is substituted for the 25 mg. of the (dl) compound of the above composition.

EXAMPLE 37

| Ingredients | Quantity per capsule, mgs. |
|---|---|
| methyl 6,11-dihydrodibenzo-[b.e.]-thiepin-11-one-3-acetate | 150 |
| lactose | 99 |

The above ingredients are mixed and introduced into a hard-shell gelatin capsule.

EXAMPLE 38

| Ingredients | Quantity per tablet, mgs. |
|---|---|
| isoamyl 6,11-dihydrodibenzo-[b.e.]-thiepin-11-one-3-acetate | 200 |
| lactose | 135 |
| magnesium stearate | 5 |

The above ingredients are mixed and pressed into single tablets.

EXAMPLE 39

| Ingredients | Quantity per tablet, mgs. |
|---|---|
| calcium 6,11-dihydrodibenzo-[b.e.]-thiepin-11-one-3-acetate | 150 |
| cornstarch (paste) | 50 |
| magnesium stearate | 0.8 |
| lactose | to 500 |

The above ingredients are thoroughly mixed and pressed into single scored tablets.

EXAMPLE 40

| Ingredients | Quantity per tablet, mgs. |
|---|---|
| potassium 6,11-dihydrodibenzo-[b.e.]-thiepin-11-one-3-acetate | 125 |
| cornstarch | 38 |

| Ingredients | Quantity per tablet, mgs. |
| --- | --- |
| magnesium stearate | 0.76 |
| polyvinylpyrrolidone | 17 |
| lactose | to 380 |

The above ingredients are mixed intimately and pressed into single scored tablets.

EXAMPLE 41

| Ingredients | Quantity per capsule, mgs. |
| --- | --- |
| Isopropylammonium 6,11-dihydrodibenzo-[b.e.]-thiepin-11-one-3-acetate | 250 |
| cornstarch | 38 |
| lactose | to 380 |

The above ingredients are mixed and introduced into a hard-shell gelatin capsule.

EXAMPLE 42

| Ingredients | Quantity per capsule, mgs. |
| --- | --- |
| isoamyl 6,11-dihydrodibenzo-[b.e.]-thiepin-11-one-3-acetate | 300 |
| lactose | 72 |
| magnesium stearate | 8 |

The above ingredients are mixed and introduced into a hard-shell gelatin capsule.

EXAMPLE 43

An injectable preparation buffered to a pH of 8.5 is prepared having the following composition:

| | |
| --- | --- |
| (dl)-2-(6,11-dihydrodibenzo-[b.e.]-thiepin-11-one-3-yl) propionic acid | 0.2 g |
| K₂HPO₄ buffer (0.4 M solution) | 2 ml. |
| KOH (1N) | 8.6 ml. |
| water (sterile) | to 20 ml. |

0.1 G. of (d)-2-(6,11-dihydrodibenzo-[b.e.]-thiepin-11-one-3-yl) propionic acid is substituted for the 0.2 g. of the (dl) compound of the above composition.

EXAMPLE 44

A suppository totaling 2.8 grams is prepared having the following composition:

| | |
| --- | --- |
| (dl)-2-(6,11-dihydrodibenzo-[b.e.]-thiepin-11-one-3-yl) propionic acid | 25 mg. |
| Witepsol H-15 (triglycerides of saturated vegetable fatty acids; a product of Riches-Nelson, Inc., New York, N.Y.) | balance |

12.5 Mg. of (d)-2-(6,11-dihydrodibenzo-[b.e.]-thiepin-11-one-3-yl) propionic acid is substituted for the 25 mg. of the (dl) compound of the above composition.

EXAMPLE 45

An oral suspension for pediatric use is prepared having the following composition:

| | |
| --- | --- |
| (dl)-2-(6,11-dihydrodibenzo-[b.e.]-thiepin-11-one-3-yl) propionic acid | 0.25 g. |
| fumaric acid | 0.5 g. |
| sodium chloride | 2.0 g. |
| methyl paraben | 0.1 g. |
| granulated sugar | 25.5 g. |
| sorbitol (70% solution) | 12.85 g. |
| Veegum K (Vanderbilt Co.) | 1.0 g. |
| flavoring | 0.035 ml. |
| colorings | 0.5 mg. |
| distilled water | to 100 ml. |

0.125 G. of (d)-2-(6,11-dihydrodibenzo-[b.e.]-thiepin-11-one-3-yl) propionic acid is substituted for the 0.25 g. of the (dl) compound of the above composition.

EXAMPLES 46–47

Powdered top dressings for veterinary use are prepared having the following compositions:

| | Ex. 46 | Ex. 47 |
| --- | --- | --- |
| (dl)-2-(6,11-dihydrodibenzo-[b.e.]-thiepin-11-one-3-yl) propionic acid | 0.2 g. | 0.4 g. |
| sucrose | 5.7 g. | 3.7 g. |
| polyvinyl pyrrolidone | 0.3 g. | 0.3 g. |

0.1 G. of (d)-2-(6,11-dihydrodibenzo-[b.e.]-thiepin-11-one-3-yl) propionic acid is substituted for the 0.2 g. of the (dl) compound of the composition of Example 46.

0.2 G. of (d)-2-(6,11-dihydrodibenzo-[b.e.]-thiepin-11-one-3-yl) propionic acid is substituted for the 0.4 g. of the (dl) compound of the composition of Example 47.

EXAMPLE 48

A suppository totaling 2.8 grams is prepared having the following composition:

| | |
| --- | --- |
| 6,11-dihydrodibenzo-[b.e.]-thiepin-11-one-3-acetic acid | 275 mg. |
| Witepsol H-15 | balance |

EXAMPLE 49

Several tests were run which simultaneously evaluated
a. phenylbutazone,
b. (dl)-2-(6,11-dihydrodibenzo-[b.e.]-thiepin-11-one-2-yl) propionic acid, and
c. (dl)-2-(6,11-dihydrodibenzo-[b.e.]-thiepin-11-one-3-yl) propionic acid,
for oral anti-inflammatory activity, utilizing carrageenin induced paw inflammation in the rat, after the method of Winter et al., Proceedings of the Society for Experimental Biology and Medicine, Vol. 111, page 544–547 (1962), as follows: Materials and Methods — Female rats weighing 80–90 grams are used. The test materials are given at hour 0 orally by gavage in 1 ml. aqueous vehicle. At hour 1, 0.05 ml. of a 1% solution (in 0.9% NaCl) of carrageenin is injected into the right hind paw. This injection causes an inflammation of the paw. The rats are sacrificed at hour 4, at which time both hind paws are removed and weighed separately.

End point: % increase in paw size calculated as follows:

$$\frac{\text{Wt. of Right Paw} - \text{Wt. of Left Paw}}{\text{Wt. of Left Paw}} \times 100$$

The data obtained, from the several tests which were run to simultaneously evaluate the compounds, was analyzed according to standard statistical procedures and the results of such analysis were as follows:

TABLE I

Oral Anti-Inflammatory Activity Of Compounds (b) and (c) Relative To Phenylbutazone, Compound (a)

| Compound | Anti-Inflammatory Activity |
| --- | --- |
| (a) phenylbutazone | 1 |
| (b) (dl)-2-(6,11-dihydrodibenzo-[b.e.]-thiepin-11-one-2-yl) propionic acid | 1.3 |
| (c) (dl)-2-(6,11-dihydrodibenzo-[b.e.]-thiepin-11-one-3-yl) propionic acid | 130 |

TABLE II

Oral Anti-Inflammatory Activity of Compound (c) Compared Directly To Compound (b)

| Compound | Anti-Inflammatory Activity |
| --- | --- |
| (b) (dl)-2-(6,11-dihydrodibenzo-[b.e.]-thiepin-11-one-2-yl) propionic acid | 1 |
| (c) (dl)-2-(6,11-dihydrodibenzo-[b.e.]-thiepin-11-one-3-yl) propionic acid | 64 |

While the present invention has been described with reference to specific embodiments thereof, it should be understood by those skilled in this art that various changes may be made and equivalents may be substituted without departing from the true spirit and scope of the invention. In addition, many modifications may be made to adapt a particular situation, material or composition of matter, process, process step of steps, or then-present objective to the spirit of this invention without departing from its essential teachings.

What is claimed is:

1. A compound of the formula:

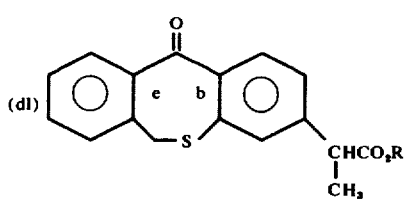

or the individual (d)-acid isomer, or (l)-acid isomer of Formula (B), wherein R is hydrogen, an alkyl group containing from one to twelve carbon atoms, or a pharmaceutically acceptable salt thereof when R is hydrogen, or the said esters and pharmaceutically acceptable salts of the individual isomers of Formula (B).

2. A compound of the formula:

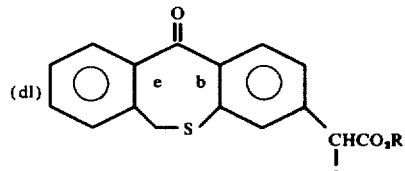

or the (d)-acid isomer thereof, wherein R is hydrogen, an alkyl group containing from one to twelve carbon atoms, or a pharmaceutically acceptable salt thereof when R is hydrogen, or the said esters and pharmaceutically acceptable salts of the (d)-acid isomer.

3. A compound of the formula:

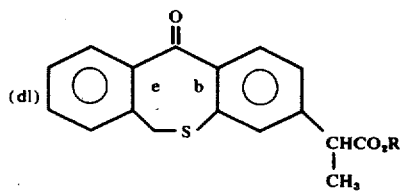

wherein R is hydrogen, an alkyl group containing from one to twelve carbon atoms, or a pharmaceutically acceptable salt thereof when R is hydrogen.

4. A compound of the formula:

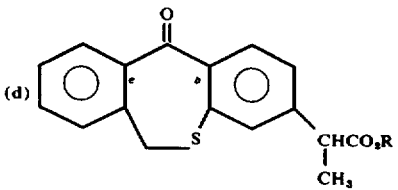

wherein R is hydrogen, an alkyl group containing from one to twelve carbon atoms, or a pharmaceutically acceptable salt thereof when R is hydrogen.

5. A compound of the formula:

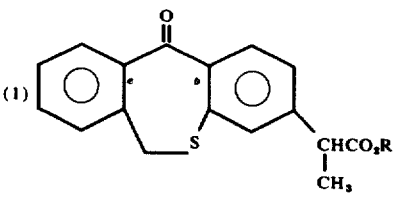

wherein R is hydrogen, an alkyl group containing from one to twelve carbon atoms, or a pharmaceutically acceptable salt thereof when R is hydrogen.

6. The (dl) compound of claim 1 wherein R is hydrogen, (dl)-2-(6,11-dihydrodibenzo-[b.e.]-thiepin-11-one-3yl) propionic acid.

7. The (dl) compound of claim 1 wherein R is methyl, methyl (dl)-2-(6,11-dihydrodibenzo-[b.e.]-thiepin-11-one-3-yl) propionate.

8. The (dl) compound of claim 1 wherein R is isoamyl, isoamyl (dl)-2-(6,11-dihydrodibenzo-[b.e.]-thiepin-11-one-3-yl) propionate.

9. The sodium salt of the (dl) compound of claim 1, sodium (dl)-2-(6,11-dihydrodibenzo-[b.e.]-thiepin-11one-3-yl) propionate.

10. The potassium salt of the (dl) compound of claim 1, potassium (dl)-2-(6,11-dihydrodibenzo-b.e.]-thiepin-11one-3-yl) propionate.

11. The calcium salt of the (dl) compound of claim 1, calcium (dl)-2-(6,11-dihydrodibenzo-[b.e.]-thiepin-11-one-3-yl) propionate.

12. The copper salt of the (dl) compound of claim 1, copper (dl)-2-(6,11-dihydrodibenzo-[b.e.]-thiepin-11-one-3-yl) propionate.

13. The piperidinium salt of the (dl) compound of claim 1, piperidinium (dl)-2-(6,11-dihydrodibenzo-[b.e.]-thiepin-11-one-3-yl) propionate.

14. The (d)isomer compound of claim 1 wherein R is hydrogen (d)-2-(6,11-dihydrodibenzo-[b.e.]-thiepin-11-one-3-yl) propionic acid.

15. The (d)-acid isomer compound of claim 1 wherein R is methyl, the methyl ester of (d)-2-(6,11-dihydrodibenzo-[b.e.]-thiepin-11one-3-yl) propionic acid.

16. The (d)-acid isomer compound of claim 1 wherein R is isoamyl, the isoamyl ester of (d)-2-(6,11-dihydrodibenzo-[b.e.]-thiepin-11-one-3-yl) propionic acid.

17. The sodium salt of the (d)-acid isomer compound of claim 1, the sodium salt of (d)-2-(6,11-dihydrodibenzo-[b.e.]-thiepin-11-one-3-yl) propionic acid.

18. The potassium salt of the (d)-acid isomer compound of claim 1, the potassium salt of (d)-2-(6,11-dihydrodibenzo-[b.e.]-thiepin-11-one-3-yl) propionic acid.

19. The calcium salt of the (d)-acid isomer compound of claim 1, the calcium salt of (d)-2-(6,11-dihydrodibenzo-[b.e.]-thiepin-11-one-3-yl) propionic acid.

20. The copper salt of the (d)-acid isomer compound of claim 1, the copper salt of (d)-2-(6,11-dihydrodibenzo-[b.e.]-thiepin-11-one-3-yl) propionic acid.

21. The piperidinium salt of the (d)-acid isomer compound of claim 1, the piperidinium salt of (d)-2-(6,11-dihydrodibenzo-[b.e.]-thiepin-11-one-3-yl) propionic acid.

22. The (1)-isomer compound of claim 1 wherein R is hydrogen, (1)-2-(6,11-dihydrodibenzo-[b.e.]-thiepin-11-one-3-yl) propionic acid.

23. Dicyclohexylammonium (dl)-2-(6,11-dihydrodibenzo-[b.e.]-thiepin-11-one-3-yl) propionate.

24. A composition for treating inflammation, pain or pyrexia in mammals consisting essentially of a pharmaceutically acceptable non-toxic excipient and a therapeutically effective amount of a compound represented by the formula:

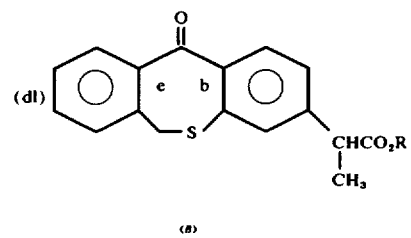

or the (d)-acid isomer of Formula (B), wherein R is hydrogen, an alkyl group containing from one to twelve carbon atoms, or a pharmaceutically acceptable salt thereof when R is hydrogen, or the said esters and pharmaceutically acceptable salts of the (d)-acid isomer.

25. A method of treating inflammation, pain or pyrexia in mammals which comprises administering to a mammal suffering therefrom a therapeutically effective amount of a compound represented by the formula:

26. A composition for administration to a pregnant mammal to delay the onset of parturition consisting essentially of a pharmaceutically acceptable non-toxic excipient and a therapeutically effective amount of a compound represented by the formula:

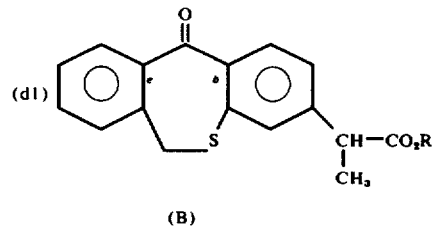

(B)

or the (d)-acid isomer of Formula (B), wherein R is hydrogen, an alkyl group containing from one to twelve carbon atoms, or a pharmaceutically acceptable salt thereof when R is hydrogen, or the said esters and pharmaceutically acceptable salts of the (d)-acid isomer.

* * * * *